US011369394B2

(12) United States Patent
Davidson et al.

(10) Patent No.: US 11,369,394 B2
(45) Date of Patent: *Jun. 28, 2022

(54) ROTATABLE CONNECTION BETWEEN AN INTERVENTION MEMBER AND A MANIPULATION MEMBER OF AN ENDOVASCULAR DEVICE

(71) Applicant: Covidien LP, Mansfield, MA (US)

(72) Inventors: James Davidson, San Juan Capistrano, CA (US); Andy Huynh, Westminster, CA (US); Kevin Nguyen, Santa Ana, CA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/709,431

(22) Filed: Dec. 10, 2019

(65) Prior Publication Data
US 2020/0113590 A1   Apr. 16, 2020

Related U.S. Application Data

(63) Continuation of application No. 14/921,223, filed on Oct. 23, 2015, now Pat. No. 10,537,344.

(51) Int. Cl.
*A61B 17/221* (2006.01)
*A61B 17/22* (2006.01)
(Continued)

(52) U.S. Cl.
CPC ...... *A61B 17/221* (2013.01); *A61B 17/22031* (2013.01); *A61B 2017/00243* (2013.01);
(Continued)

(58) Field of Classification Search
CPC ............ A61B 17/22031; A61B 17/221; A61B 2017/00243; A61B 2017/00477;
(Continued)

(56) References Cited

U.S. PATENT DOCUMENTS 7,300,458 B2   11/2007   Henkes et al.
7,306,618 B2   12/2007   Demond et al.
(Continued)

FOREIGN PATENT DOCUMENTS

EP   1346703 A1   9/2003
EP   2319575 B1   11/2013
(Continued)

OTHER PUBLICATIONS

International Search Report and Written Opinion dated Dec. 16, 2016; International Application No. PCT/US2016/057864; 12 pages.

*Primary Examiner* — Brooke Nicole Labranche
(74) *Attorney, Agent, or Firm* — Fortem IP LLP; Katrina Marcelo; Matthew Linicum

(57) ABSTRACT

A medical device, configured to perform an endovascular therapy, e.g., thrombectomy, can comprise an elongate manipulation member having a first connection member proximate a distal end of the elongate manipulation member, and an intervention member having a second connection member proximate a proximal end of the intervention member. The second connection member can be connected to the first connection member such that the first connection member can rotate relative to the second connection member.

22 Claims, 30 Drawing Sheets

(51) Int. Cl.
  *A61B 17/00* (2006.01)
  *A61B 17/12* (2006.01)
(52) U.S. Cl.
  CPC .............. *A61B 2017/00477* (2013.01); *A61B 2017/12054* (2013.01); *A61B 2017/2215* (2013.01); *A61B 2017/22034* (2013.01)
(58) Field of Classification Search
  CPC   A61B 2017/12054; A61B 2017/22034; A61B 2017/2215; A61B 2017/22035
  See application file for complete search history.

(56) References Cited

U.S. PATENT DOCUMENTS

| | | |
|---|---|---|
| 7,648,518 B2 | 1/2010 | Salahieh et al. |
| 8,092,508 B2 | 1/2012 | Leynov et al. |
| 8,603,014 B2 | 12/2013 | Alleman et al. |
| 8,777,978 B2 | 7/2014 | Strauss et al. |
| 8,837,800 B1 | 9/2014 | Bammer et al. |
| 8,968,383 B1 | 3/2015 | Johnson et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0018596 A1* | 8/2001 | Selmon ............... A61M 29/02 606/198 |
| 2007/0162048 A1 | 7/2007 | Quinn et al. |
| 2008/0188886 A1 | 8/2008 | Kusleika et al. |
| 2009/0082800 A1 | 3/2009 | Janardhan |
| 2010/0137898 A1 | 6/2010 | Teoh |
| 2011/0004238 A1 | 1/2011 | Palmer et al. |
| 2011/0060212 A1 | 3/2011 | Slee et al. |
| 2011/0160763 A1 | 6/2011 | Ferrera et al. |
| 2012/0071916 A1 | 3/2012 | Kusleika et al. |
| 2012/0083868 A1 | 4/2012 | Shrivastava et al. |
| 2012/0172920 A1 | 7/2012 | Fifer et al. |
| 2013/0030461 A1 | 1/2013 | Marks et al. |
| 2013/0281788 A1 | 10/2013 | Garrison |
| 2013/0345739 A1 | 12/2013 | Brady et al. |
| 2014/0194911 A1 | 7/2014 | Johnson et al. |
| 2014/0194919 A1 | 7/2014 | Losordo et al. |
| 2014/0276074 A1 | 9/2014 | Warner |
| 2014/0343595 A1 | 11/2014 | Monstadt et al. |
| 2015/0039017 A1 | 2/2015 | Cragg et al. |
| 2015/0080937 A1 | 3/2015 | Davidson |
| 2015/0100113 A1 | 4/2015 | Davidson et al. |
| 2015/0133990 A1 | 5/2015 | Davidson |
| 2015/0359547 A1 | 12/2015 | Vale et al. |
| 2016/0015402 A1 | 1/2016 | Brady et al. |
| 2016/0015935 A1 | 1/2016 | Chan et al. |
| 2016/0030047 A1 | 2/2016 | Allen et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| JP | 2014004219 A | 1/2014 |
| JP | 2018118132 A | 8/2018 |
| KR | 20180102877 A | 9/2018 |
| WO | 2014109840 A1 | 7/2014 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

* cited by examiner

ROTATABLE CONNECTION BETWEEN AN INTERVENTION MEMBER AND A MANIPULATION MEMBER OF AN ENDOVASCULAR DEVICE

CROSS-REFERENCE TO RELATED APPLICATIONS

This application is a continuation of U.S. patent application Ser. No. 14/921,223, filed Oct. 23, 2015, which is incorporated herein by reference in its entirety.

BACKGROUND

Blood vessels can become occluded by emboli, e.g., thrombi. For example, intracranial arteries can become occluded by thromboembolisms. Disruption of blood flow by the occlusion can prevent oxygen and nutrients from being delivered to tissues downstream of the occlusion. Deprivation of oxygen and nutrients to tissue distal to an occlusion can impair proper function of the tissue, and may result in cellular death. Cellular death increases with duration of the occlusion.

SUMMARY

The curvature of a blood vessel within which a medical device for endovascular intervention is being delivered can result in rotation of the medical device as it is moved through the blood vessel. An aspect of at least some of the embodiments disclosed herein involves the recognition that the extent of rotation of an intervention member engaged with a thrombus, relative to a vessel from which the thrombus is being retrieved and about a longitudinal axis of the vessel, can affect the likelihood of successful thrombus retrieval, a risk or extent of damage to a wall of the vessel during thrombus retrieval, or both.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 13, 25, or 38. The other clauses can be presented in a similar manner.

1. A medical device configured to perform an endovascular therapy, the device comprising:
   an elongate manipulation member having a first connection member proximate a distal end of the elongate manipulation member; and
   an intervention member having a second connection member, the second connection member connected to the first connection member such that the first connection member can rotate relative to the second connection member within a non-infinite rotation range without deformation of any of the first connection member or the second connection member.
2. The medical device of Clause 1, wherein the second connection member is connected to the first connection member such that the first connection member can rotate relative to the second connection member within the non-infinite rotation range of at least 360° without plastic deformation of any of the first connection member or the second connection member.
3. The medical device of Clause 1, wherein the second connection member is connected to the first connection member such that the first connection member can rotate relative to the second connection member within the non-infinite rotation range of at least 360° with neither resistance nor restriction within the medical device apart from friction.
4. The medical device of Clause 1, wherein the first connection member comprises a first loop, and the second connection member comprises a second loop.
5. The medical device of Clause 4, wherein the second connection member is connected to the first connection member by at least a third loop.
6. The medical device of Clause 5, wherein the third loop passes through openings in each of the first and second loops.
7. The medical device of Clause 1, wherein the second connection member is connected to the first connection member by a third connection member.
8. The medical device of Clause 7, wherein the third connection member connects first and second connection members such that the first connection member can rotate relative to the second connection member within the non-infinite rotation range of at least 360° without deformation of the third connection member.
9. The medical device of Clause 1, wherein the first connection member and the elongate manipulation member are integrally formed as a single monolithic component.
10. The medical device of Clause 1, wherein the first connection member is discrete from the elongate manipulation member.
11. The medical device of Clause 1, wherein the second connection member and the intervention member are integrally formed as a single monolithic component.
12. The medical device of Clause 1, wherein the second connection member is discrete from the intervention member.
13. A medical device configured to perform an endovascular therapy, the device comprising:
    an elongate manipulation member having a first connection member proximate a distal end of the elongate manipulation member; and
    an intervention member having a second connection member, the second connection member connected to the first connection member such that the first connection member can rotate relative to the second connection member within a non-infinite rotation range of at least 360° without deformation of any of the first connection member or the second connection member.
14. The medical device of Clause 13, wherein the second connection member is connected to the first connection member such that the first connection member can rotate relative to the second connection member within the non-infinite rotation range of at least 360° without plastic deformation of any of the first connection member or the second connection member.
15. The medical device of Clause 13, wherein the second connection member is connected to the first connection member such that the first connection member can rotate relative to the second connection member within the non-infinite rotation range of at least 360° with neither resistance nor restriction within the medical device apart from friction.
16. The medical device of Clause 13, wherein the first connection member comprises a first loop, and the second connection member comprises a second loop.

17. The medical device of Clause 16, wherein the second connection member is connected to the first connection member by at least a third loop.
18. The medical device of Clause 17, wherein the third loop passes through openings in each of the first and second loops.
19. The medical device of Clause 13, wherein the second connection member is connected to the first connection member by a third connection member.
20. The medical device of Clause 19, wherein the third connection member connects first and second connection members such that the first connection member can rotate relative to the second connection member within the non-infinite rotation range of at least 360° without deformation of the third connection member.
21. The medical device of Clause 13, wherein the first connection member and the elongate manipulation member are integrally formed as a single monolithic component.
22. The medical device of Clause 13, wherein the first connection member is discrete from the elongate manipulation member.
23. The medical device of Clause 13, wherein the second connection member and the intervention member are integrally formed as a single monolithic component.
24. The medical device of Clause 13, wherein the second connection member is discrete from the intervention member.
25. A medical device for removal of an occlusive thrombus from a blood vessel, the device comprising:
    an elongate manipulation member having a first connection member proximate a distal end of the elongate manipulation member; and
    an intervention member having a self-expanding structure and a second connection member, the self-expanding structure having a plurality of cells, the self-expanding tubular structure being compressible to a collapsed configuration for delivery to an endovascular treatment site through a catheter and being self-expandable from the collapsed configuration to an expanded configuration, the plurality of cells sized to penetrate into and capture thrombus upon expansion to the expanded configuration, the second connection member connected to the first connection member such that the first connection member can rotate relative to the second connection member without deformation of any of the first connection member or the second connection member.
26. The medical device of Clause 25, wherein the second connection member is connected to the first connection member such that the first connection member can rotate relative to the second connection member within a non-infinite rotation range without deformation of any of the first connection member or the second connection member.
27. The medical device of Clause 26, wherein the non-infinite rotation range is at least 360°.
28. The medical device of Clause 25, wherein the second connection member is connected to the first connection member such that the first connection member can rotate relative to the second connection member within the non-infinite rotation range without plastic deformation of any of the first connection member or the second connection member.
29. The medical device of Clause 25, wherein the second connection member is connected to the first connection member such that the first connection member can rotate relative to the second connection member within the non-infinite rotation range with neither resistance nor restriction within the medical device apart from friction.
30. The medical device of Clause 25, wherein the first connection member comprises a first loop and the second connection member comprises a second loop.
31. The medical device of Clause 30, wherein the second connection member is connected to the first connection member by at least a third loop.
32. The medical device of Clause 31, wherein the third loop passes through openings in each of the first and second loops.
33. The medical device of Clause 25, wherein the first and second connection members comprise a ball joint.
34. The medical device of Clause 33, wherein the first connection member comprises a ball and the second connection member comprises a socket.
35. The medical device of Clause 25, wherein the first and second connection members comprise a universal joint.
36. The medical device of Clause 25, wherein the second connection member is connected to the first connection member by a third connection member.
37. The medical device of Clause 36, wherein the third connection member connects first and second connection members such that such that the first connection member can rotate relative to the second connection member within the non-infinite rotation range of without deformation of the third connection member.
38. A method for removal of thrombus from a blood vessel, the method comprising:
    delivering a medical device to a treatment site within a blood vessel radially adjacent a thrombus, the device comprising:
        an elongate manipulation member comprising a first connection member proximate a distal end of the elongate manipulation member; and
        an intervention member comprising a self-expanding structure and a second connection member, the self-expanding structure being compressible to a collapsed configuration for delivery to an endovascular treatment site through a catheter and being self-expandable from the collapsed configuration to an expanded configuration, the second connection member connected to the first connection member;
    expanding the device into the thrombus;
    capturing the thrombus with the self-expanding structure;
    pulling proximally the elongate manipulation member to retract the self-expanding structure within the blood vessel while the first connection member rotates relative to the second connection member within a rotation range without deformation of any of the first connection member or the second connection member.
39. The method of Clause 38, wherein the rotation range is at least 360°.
40. The method of Clause 38, wherein the first connection member rotates relative to the second connection member within the rotation range without plastic deformation of any of the first connection member or the second connection member.
41. The method of Clause 38, wherein the first connection member rotates relative to the second connection member within the rotation range with neither resistance nor restriction within the medical device apart from friction.

42. The method of Clause 38, wherein the first connection member comprises a first loop, and the second connection member comprises a second loop, and wherein the first loop rotates relative to the second loop while pulling proximally the elongate manipulation member to retract the self-expanding structure within the blood vessel.
43. The method of Clause 42, wherein the second connection member is connected to the first connection member by at least a third loop, and wherein the third loop rotates relative to at least one of the first loop and the second loop while pulling proximally the elongate manipulation member to retract the self-expanding structure within the blood vessel.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology may be practiced without these specific details. In some instances, well-known structures and components are shown in block diagram form in order to avoid obscuring the concepts of the subject technology.

Figure 1:
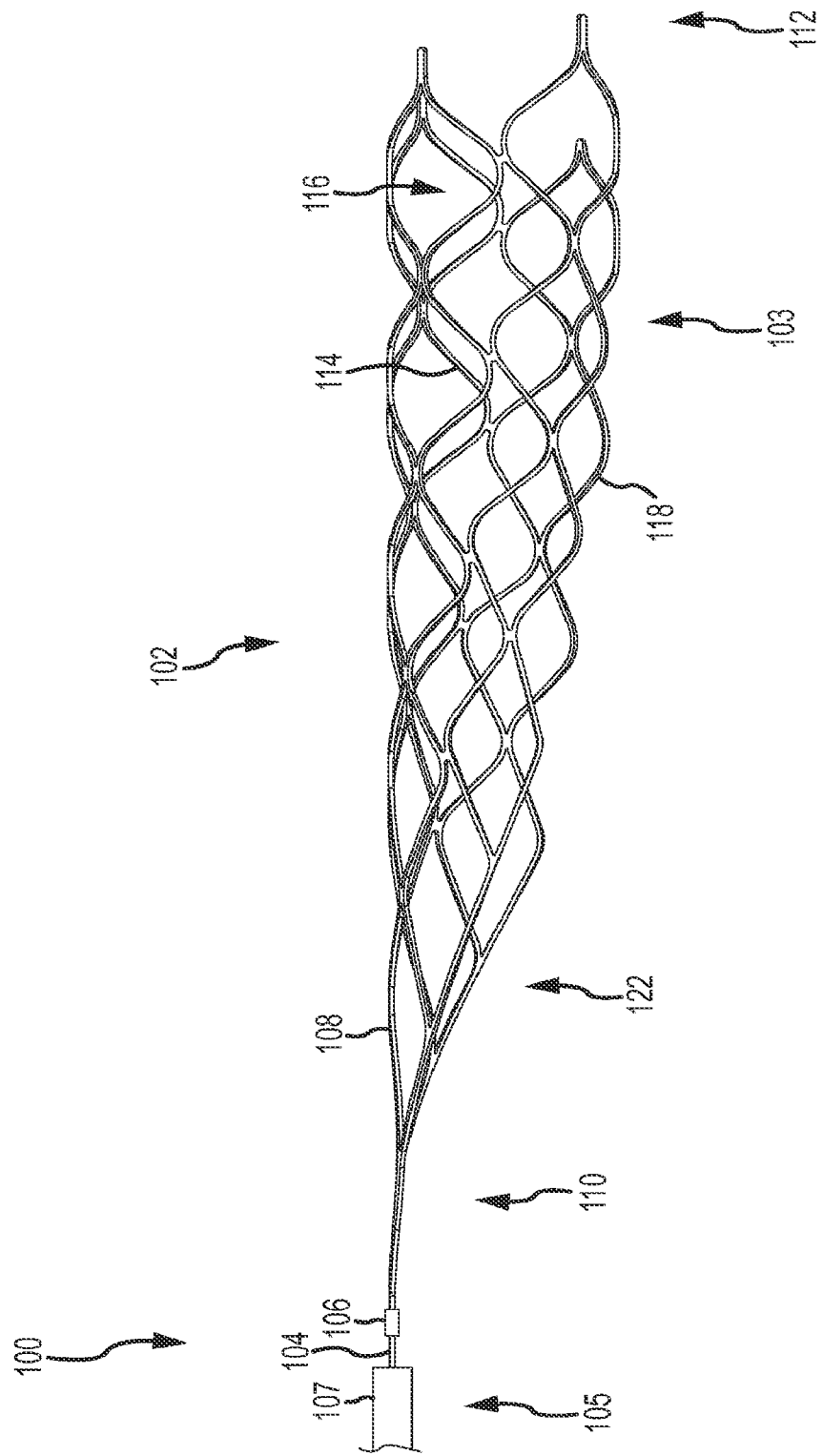
FIG. 1 illustrates a device, including an intervention member, for blood flow restoration, thrombus removal, or both, according to an embodiment.

FIG. 1 depicts a medical device 100 according to some embodiments of the subject technology. As illustrated in FIG. 1, the medical device 100 can comprise an intervention member 102 and a manipulation member 104. The intervention member 102 may comprise an expandable member 103. A proximal end portion of the intervention member 102 and a distal end portion of the manipulation member 104 can be joined at a connection 106. The manipulation member 104 can extend through a catheter 107 such that an operator can manipulate the intervention member 102, positioned within and/or distal to a distal end of the catheter 107, using the manipulation member 104 at a location proximal to a proximal end of the catheter 107.

The manipulation member 104 can be elongate. The manipulation member 104 can have a length sufficient to extend from a location outside the patient's body through the vasculature to a treatment site within the patient's body. For example, the manipulation member can have a length of at least 100 cm, at least 130 cm, or at least 150 cm. The manipulation member 104 can be monolithic or formed of multiple joined components. In some embodiments, the manipulation member 104 can comprise a combination of wire(s), coil(s), and/or tube(s). The manipulation member 104 can comprise one or more markers, e.g., comprised of radiopaque material(s) to aid radiographic visualization during manipulation.

The intervention member 102 and the manipulation member 104 can be attached together at the connection 106. In some embodiments, the intervention member 102 and the manipulation member 104 can be substantially permanently attached together at the connection 106. That is, the intervention member 102 and the manipulation member 104 can be attached together in a manner such that, under the expected use conditions of the medical device 100, the endovascular device and the manipulation member would not become separated, whether deliberately or unintentionally, from one another without damage to or destruction of at least a portion of the connection 106. In some embodiments, the intervention member 102 and the manipulation member 104 can be permanently or releasably attached together at the connection 106.

Depending on the procedure and intended use of the medical device 100, it optionally may be advantageous to have a connection mechanism that permits intentional release of the intervention member 102. For example, during a blood flow restoration procedure, it may prove difficult and/or dangerous to fully retrieve a thrombus due to a complicated vasculature or the risk of damaging a lumen wall. Leaving the intervention member 102 inside the patient may prove to be the only option available to a surgeon or other medical personnel, or it may be a goal of the procedure, such as when the intervention member 102 is deployed across an aneurysm (e.g., as an aneurysm bridge to retain coils or other materials in an aneurysm). In other circumstances the intervention member 102 may include drug-eluting capabilities, and/or may be coated with a particular type of drug that facilitates thrombus dissolution. It may be advantageous in such circumstances to release the intervention member 102 and allow the intervention member 102 to anchor the thrombus against the lumen wall while the thrombus is dissolved by the drug. In some embodiments, the medical device 100 can comprise a portion, located proximally or distally of the connection 106, that is configured for selective detachment of the intervention member 102 from the manipulation member 104. For example, such a portion can comprise an electrolytically severable or mechanically detachable segment of the manipulation member. In some embodiments, the medical device 100 can be devoid of any feature that would permit selective detachment of the intervention member 102 from the manipulation member 104.

In some embodiments, the connection 106 is configured to permit rotation of a distal end of the manipulation member 104 relative to a proximal end of the intervention member 102 about an axis parallel to, generally parallel to, or coincident with a portion of a longitudinal axis of the medical device 100, the intervention member 102, the manipulation member 104, or an anatomical vessel. The connection 106 can be configured to permit such relative rotation over an infinite or a non-infinite range of rotation angles and directions. In some embodiments, connection 106 can be configured to permit such relative rotation of at least 360°. In some embodiments, the connection 106 can be configured to permit such relative rotation without deformation of one or both of the intervention member 102 and the manipulation member 104. In some such embodiments, the connection 106 can be configured to permit the relative rotation over the range of rotation angles without plastic deformation of one or both of the intervention member 102 and the manipulation member 104. In some embodiments, the connection 106 can be configured to permit the relative rotation without one or both of resistance and restriction within the medical device 100, apart from friction.

Figure 2:
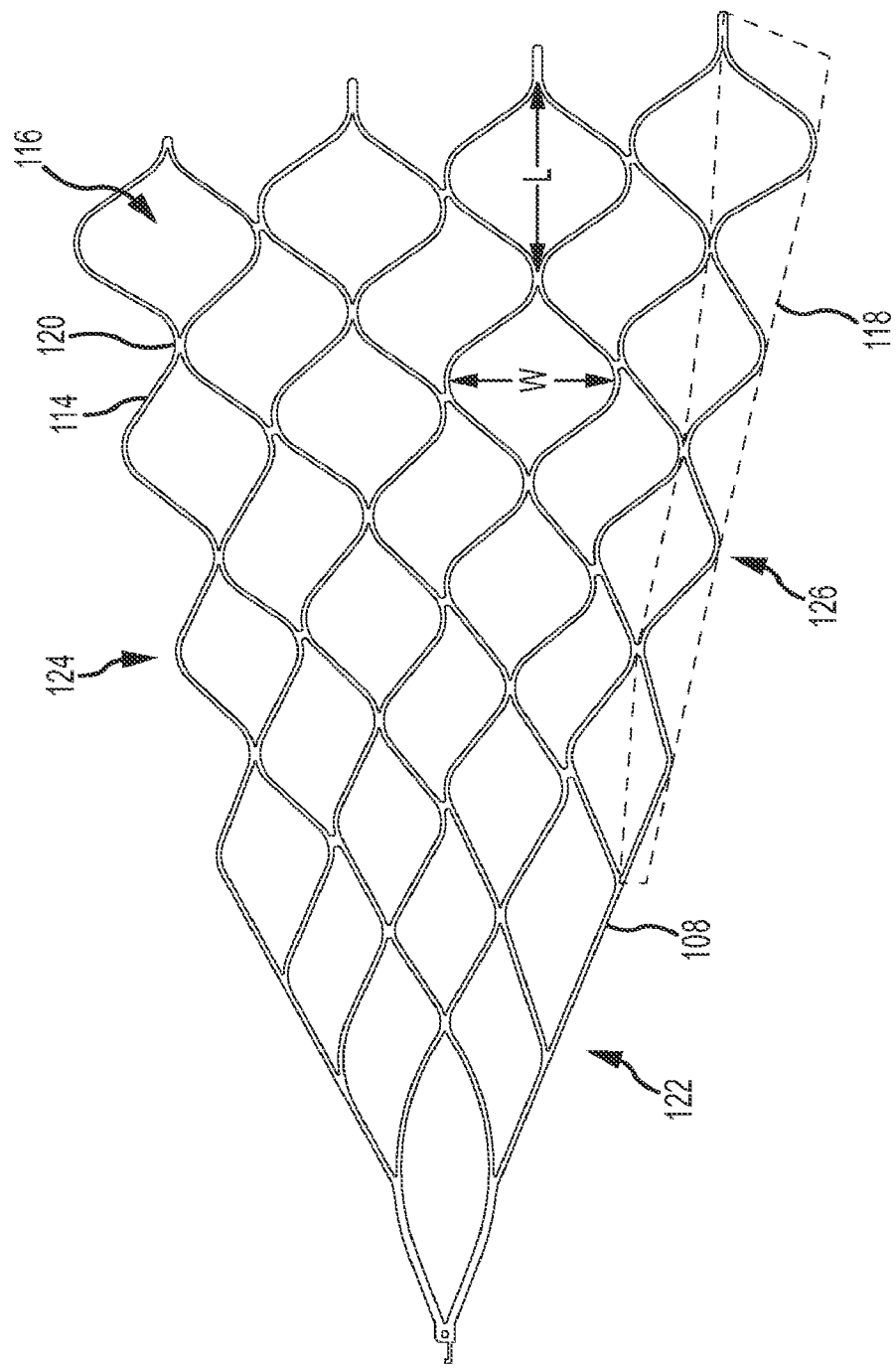
FIG. 2 illustrates an intervention member, according to an embodiment, in an unrolled state.
Figure 3:
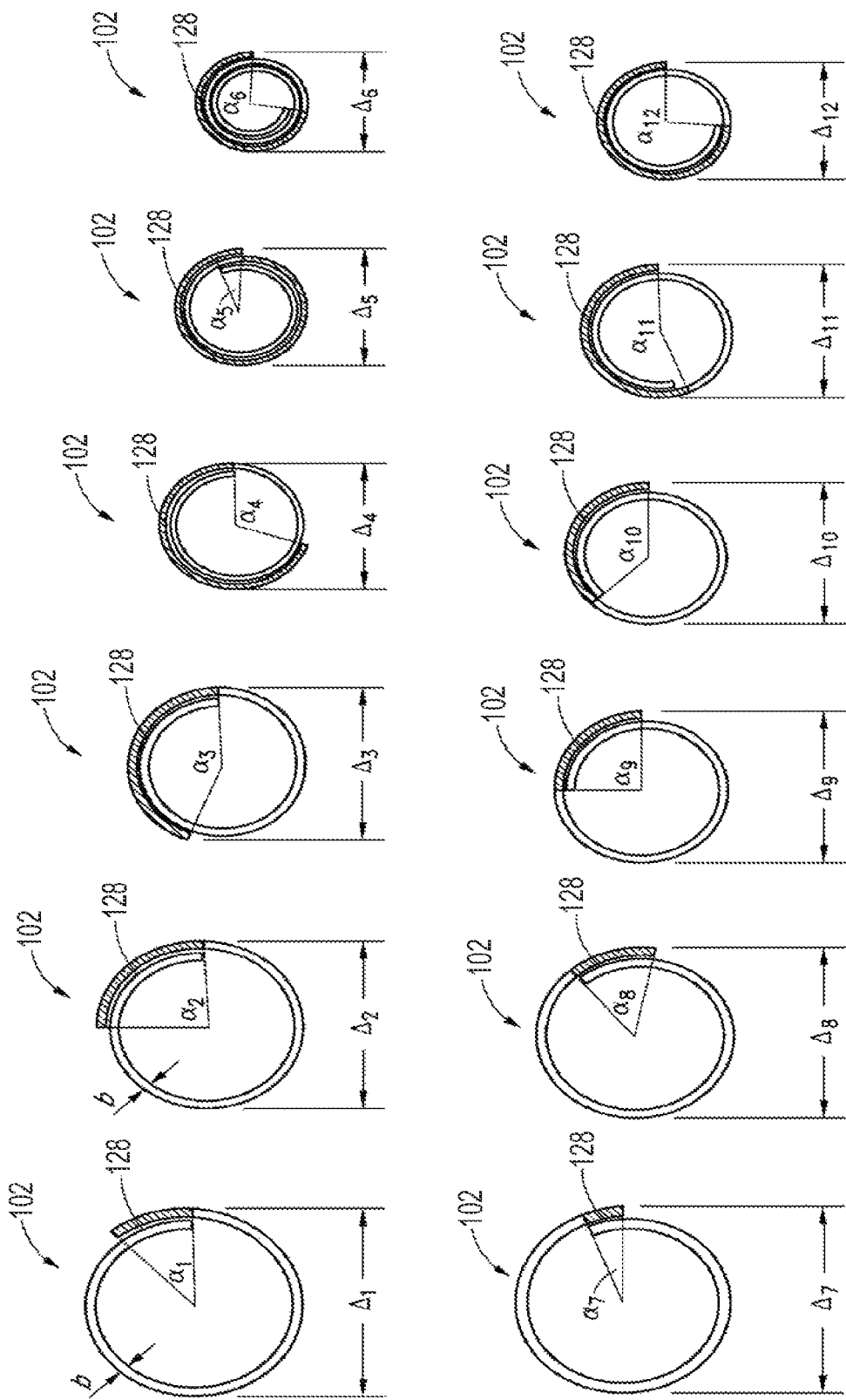
FIG. 3 is a schematic illustration of overlap configurations of the intervention member of FIG. 2, as viewed from a distal end of the intervention member.
Figure 4A:
FIGS. 4A-D are schematic illustrations of overlap configurations of the intervention member of FIG. 2.
Figure 4B:
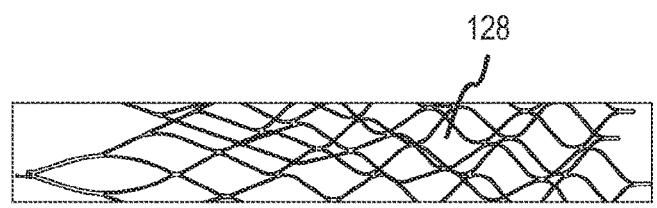
Figure 4C:
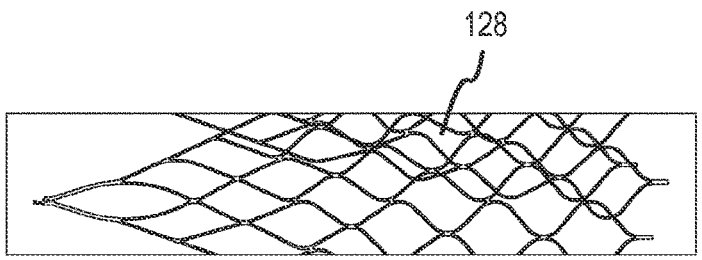
Figure 4D:
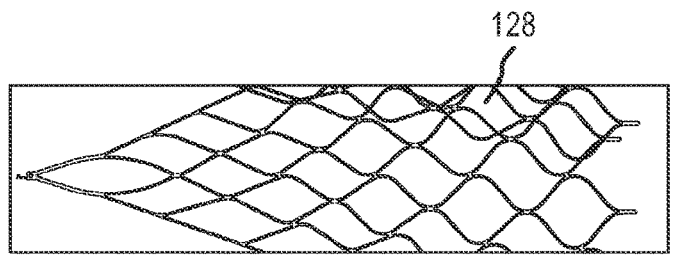

FIG. 2 is a plan view showing one embodiment of the intervention member 102 in an unrolled state to facilitate description and understanding. As illustrated in FIGS. 1 and 3, the intervention member 102 can have a tubular or generally cylindrical shape in absence of external forces in some embodiments. The intervention member 102 can be self-expanding, e.g. by super-elasticity or shape memory, or expandable in response to forces applied on the expandable member, e.g. by a balloon.

As illustrated in FIGS. 1 and 2, the intervention member 102 can comprise a frame 108 having a proximal end 110 and a distal end 112. The frame can comprise a plurality of struts 114 and a plurality of cells 116 forming a mesh. Groups of longitudinally and serially interconnected struts 114 can form undulating members 118 that extend in a generally longitudinal direction. The struts 114 can be connected to each other by joints 120. While the struts are shown having a particular undulating or sinuous configurations, in some embodiments the struts can have other configurations. The frame can have a generally tubular or generally cylindrical shape with one or both of the proximal end 110 and the distal end 112 being open. In some embodiments, the frame can have a shape that is neither tubular nor cylindrical.

As illustrated in FIGS. 1 and 2, a proximal portion 122 of the intervention member 102 can be tapered toward the proximal end 110. In some embodiments, the taper of the proximal portion can advantageously facilitate retraction and repositioning of the medical device 100 and intervention member 102. In some embodiments, the tapered proximal portion can also be designed to generally not contact the vessel wall during a blood flow restoration procedure, and to generally not interfere with the flow of blood within a vessel.

Individual cells of the proximal portion 122 can have different sizes than individual cells located distal to the tapered proximal portion. For example, in some embodiments, the proximal portion 122 can have individual cells that have a size larger than that of the individual cells located distal to the tapered proximal portion. The proximal portion 122 can taper gradually towards the connection 106.

The taper of proximal portion 122 can be at various angles relative to the manipulation member 104 or the longitudinal axis of the intervention member 102. For example, in some embodiments, the taper can have an angle of approximately 45 degrees relative to the manipulation member, though other angles are also possible, and within the scope of the present disclosure.

The intervention member 102 can comprise a first edge 124 and a second edge 126. The first edge 124 and second edge 126 can be formed, for example, from cutting a sheet or a tube. While the first and second edges are shown as having an undulating, or sinuous configuration, in some embodiments the first and second edges can have a straight, or linear configuration, or other configuration. In some embodiments, the edges 124, 126 can be curved, straight, or a combination thereof along the tapered proximal portion 122.

Referring to FIGS. 3 and 4A-D, the intervention member 102 in some embodiments can be curled, rolled, or otherwise formed such that first edge 124 and second edge 126 overlap one another when the intervention member 102 is in a volume-reduced form. In a volume-reduced form, the frame 108 of the intervention member 102 can overlap to facilitate introduction of the intervention member 102 into and through the catheter 107. In some embodiments, the intervention member 102 is circumferentially continuous (e.g., forming a continuous cylindrical shape), lacking first and second edges 124, 126 and having no overlap or gap in a volume-reduced form and expanded form. Regardless of whether the expandable member is circumferentially continuous, the intervention member 102 can have a central longitudinal axis both while in a volume-reduced form and when fully or partially expanded. In some embodiments, the intervention member 102 can be self-expandable, and can expand toward a fully expanded configuration upon release from the catheter 107. Upon expansion, the intervention member 102 can expand towards an inner wall of a vessel, towards an occlusive or partially-occlusive thrombus within a vessel, or both.

FIGS. 3 and 4A-4D illustrate various amounts of overlap of the frame 108 of the intervention member 102. The extent of any overlap of the frame 108 can depend upon a degree of the frame's expansion. Expansion within a vessel can be limited, at least in part, by the vessel's size, and the amount and the properties of any thrombus present. For example, a greater overlap of the edges 124, 126 can occur in narrower vessels, whereas in wider vessels the overlap can be smaller, or even an "underlap" may occur, in which case the edges 124 and 126 are separated by an open gap or space within the vessel.

With continued reference to FIGS. 3 and 4A-D, embodiments of the intervention member 102 can experience various degrees of overlap in a volume-reduced form, forming zones of overlap 128. The intervention member 102 can assume various diameters $\Delta_1$, $\Delta_2$, etc., depending on the degree of the overlap (e.g. represented by angle $\alpha_1$, $\alpha_2$, etc.). As illustrated in FIGS. 4A-D, the overlap zones 128 can vary in size and configuration depending on the vessel size. When inside a vessel, the overlap zone of the intervention member 102 can advantageously provide grip and/or retaining ability with respect to a thrombus. For example, when the intervention member 102 expands against a thrombus, the individual struts 114 and individual cells 116 of the overlap zone can embed into and grip, or retain, the thrombus. Alternatively, the intervention member 102 can be constructed without any overlap or edges 124, 126, e.g. as a continuous tubelike or cylindrical member.

Upon intervention member 102 expansion into an expanded configuration, the individual cells 116 can be sized to penetrate into a thrombus, capture a thrombus, or both. In some embodiments, the intervention member 102 can capture the thrombus with the individual cells 116 and/or with an exterior, or radial exterior, of the expanded intervention member 102. Further, in other embodiments, the intervention member 102 may capture or engage with a portion of the thrombus with individual cells 116 and/or an exterior, or radial exterior, of the expanded intervention member 102.

The intervention member 102 can be manufactured in various lengths and relaxed-state diameters. In some embodiments, the intervention member 102 can have lengths, measured proximally to distally along the longitudinal axis, of 15 mm or less to 40 mm or more, though other ranges and sizes are also possible. The intervention member 102 can also have relaxed-state diameters, the diameters being measured when the intervention member 102 is fully free to expand, i.e., in absence of external forces. In some embodiments, the intervention member 102 can have a diameter of approximately 3 mm to 4 mm so as to be used in size 18 microcatheters (i.e. microcatheters with an inner diameter of approximately 0.21 inch). In some embodiments the intervention member 102 can have a diameter of approximately 5 mm to 6 mm so as to be used in size 27 microcatheters (i.e. microcatheters with an inner diameter of approximately 0.027 inch). Other ranges and values are also possible.

Each cell 116 of the intervention member 102 can have a maximum length (labeled "L" in FIG. 2), as measured along a longitudinal axis of the intervention member 102, and a maximum width W, as measured along a direction generally perpendicular to the length (labeled "W" in FIG. 2). In some embodiments, cell size and dimensions can vary, as can the individual filament thicknesses and widths.

Further details regarding intervention members 102 and manipulation members 104, as well as other types of intervention members 102, are disclosed in U.S. Pat. No. 7,300,458, entitled Medical Implant Having a Curable Matrix Structure, issued Nov. 27, 2007; U.S. Patent Application Publication No. 2011/0060212, entitled Methods and Apparatus for Flow Restoration, published on Mar. 10, 2011; U.S. Patent Application Publication No. 2012/0083868, entitled Methods and Apparatuses for Flow Restoration and Implanting Members in the Human Body, published on Apr. 5, 2012; U.S. Patent Application Publication No. 2011/0160763, entitled Blood Flow Restoration in Thrombus Management Methods, published on Jun. 30, 2011; U.S. Patent Application Publication No. 2014/0194919, entitled Connection of an Endovascular Intervention Device to a Manipulation Member, published on Jul. 10, 2014; U.S. Patent Application Publication No. 2014/0194911, entitled Connection of a Manipulation Member, Including a Bend without Substantial Surface Cracks, to an Endovascular Intervention Device, published on Jul. 10, 2014; U.S. Patent Application Publication No. 2015/0080937, entitled Endovascular Device Engagement, published on Mar. 19, 2015; and U.S. Patent Application Publication No. 2015/0133990, entitled Galvanically Assisted Attachment of Medical Devices to Thrombus, published on May 14, 2015; the entirety of each of which is hereby incorporated by reference herein.

Figure 5:
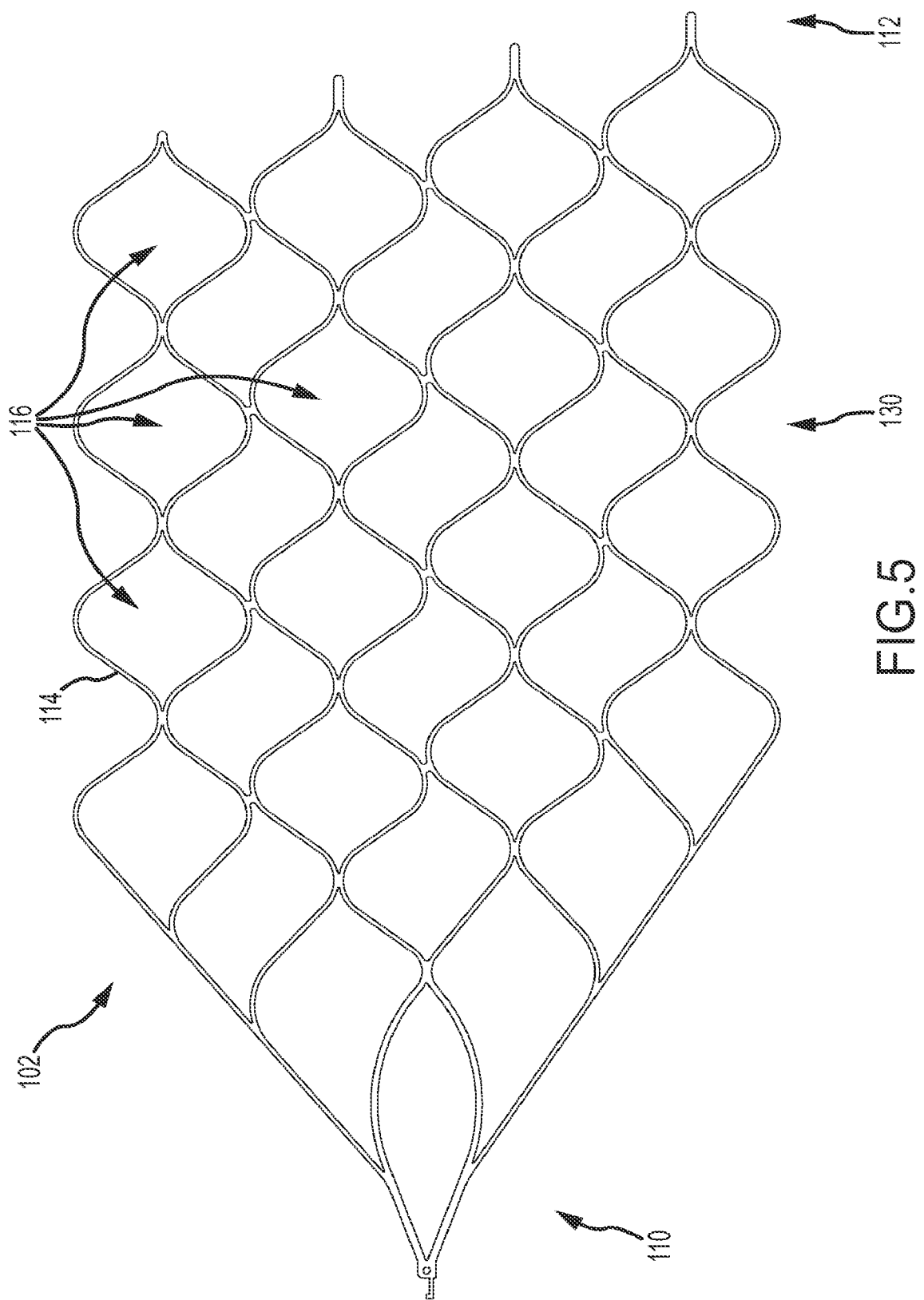
FIG. 5 illustrates an intervention member in an unrolled state.

FIG. 5 illustrates an embodiment of the intervention member 102 having a pattern 130 of cells 116 of substantially uniform dimensions and struts 114 of substantially uniform dimensions.

Figure 6:
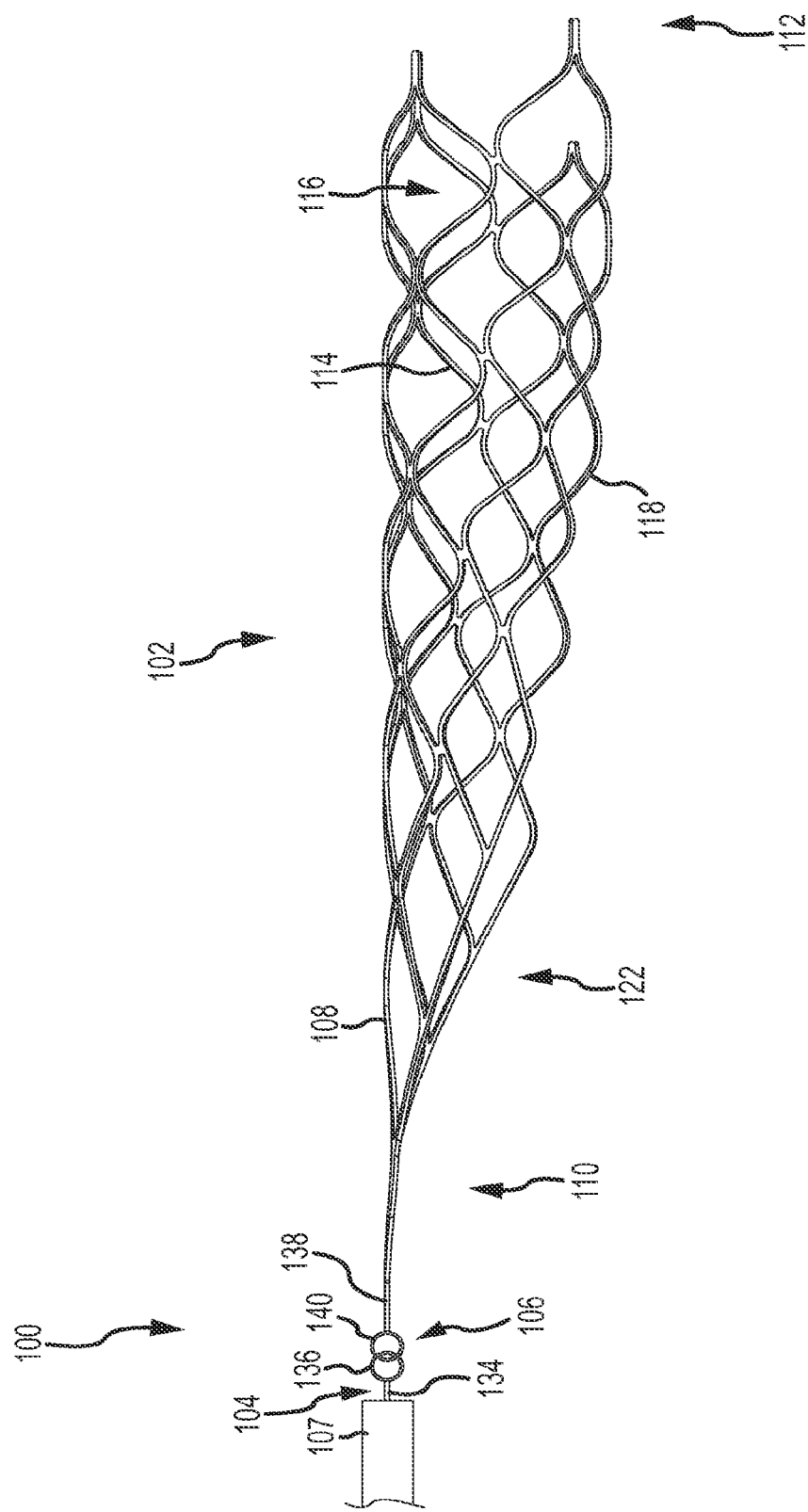
FIGS. 6 and 7 illustrate embodiments of a connection between an intervention member and a manipulation member that allows relative rotation therebetween.

FIG. 6 illustrates an embodiment wherein the connection 106 comprises a first connection member 136 and a second connection member 140. As illustrated in FIG. 6, the manipulation member 104 can have the distal manipulation member end 134, and the distal manipulation member end portion 134 can have the first connection member 136. In some embodiments, the distal manipulation member end portion 134 can comprise the first connection member 136 and, in other embodiments, the first connection member 136 can be attached to the distal manipulation member end portion 134. As further illustrated in FIG. 6, the intervention member 102 can have a proximal intervention member end portion 138, and the proximal intervention member end portion 138 can have the second connection member 140. In some embodiments, the proximal intervention member end portion 138 can comprise the second connection member 140 and, in other embodiments, the second connection member 140 can be attached to the proximal intervention member end portion 138.

The first connection member 136 and the manipulation member 104 can be integrally formed as a single monolithic component. In other embodiments, the first connection member 136 and the manipulation member 104 can be formed as discrete elements, and subsequently connected to each other. Similarly, the second connection member 140 and the intervention member 102 can be integrally formed as a single monolithic component. In other embodiments, the second connection member 140 and the intervention member 102 can be formed as discrete elements, and subsequently connected to each other.

The first connection member 136 and the second connection member 140 can be connected, directly or indirectly. In some embodiments, the first connection member 136 can rotate relative to the second connection member 140 (or vice versa, or both) about an axis parallel to, generally parallel to, or coincident with a portion of a longitudinal axis of the medical device 100, the intervention member 102, the manipulation member 104, or an anatomical vessel. Such relative rotation can be enabled over an infinite or a non-infinite range. In some embodiments, the connection 106 can be configured to permit such relative rotation of at least 360°. In some embodiments, the first connection member 136 and the second connection member 140 can relatively rotate without deformation of one or both of the first connection member 136 and the second connection member 140. In some embodiments, the first connection member 136 and the second connection member 140 can relatively rotate without plastic deformation of one or both of the first connection member 136 and the second connection member 140. In some embodiments, the first connection member 136 and the second connection member 140 can relatively rotate without one or both of resistance and restriction within the medical device 100, e.g., between the first connection member 136 and the second connection member 140, apart from friction.

Figure 8:
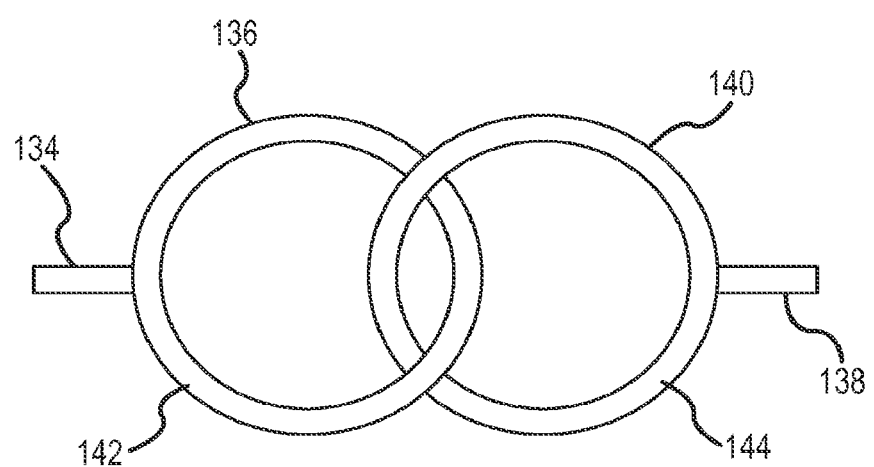
FIGS. 8 and 9 are schematic enlarged views of the connections of FIGS. 6 and 7, respectively.

The first connection member 136 can comprise a first loop 142 and the second connection member 140 can comprise a second loop 144, as illustrated, for example, in FIGS. 6 and 8. The first loop 142 and the second loop 144 can each be continuous and closed. The first loop 142 and the second loop 144 can comprise a variety of shapes, such as, for example, circular, oval, teardrop, or polygonal, and optionally be formed as a generally rigid hoop or ring having any such shape. In some embodiments, the first loop 142 can have the same shape as has the second loop 144. In some embodiments, the first loop 142 can have a different shape than has the second loop 144. In some embodiments, such as the embodiment illustrated in FIGS. 6 and 8, the first loop 142 and the second loop 144 can be circular or substantially or nominally circular in shape. In some embodiments, the first loop 142 and the second loop 144 can comprise various alloys, metals and/or composite materials. In some embodiments, the first loop 142 and the second loop 144 can be rigid, e.g., more rigid than a loop formed by a thin polymer filament.

Figure 7:
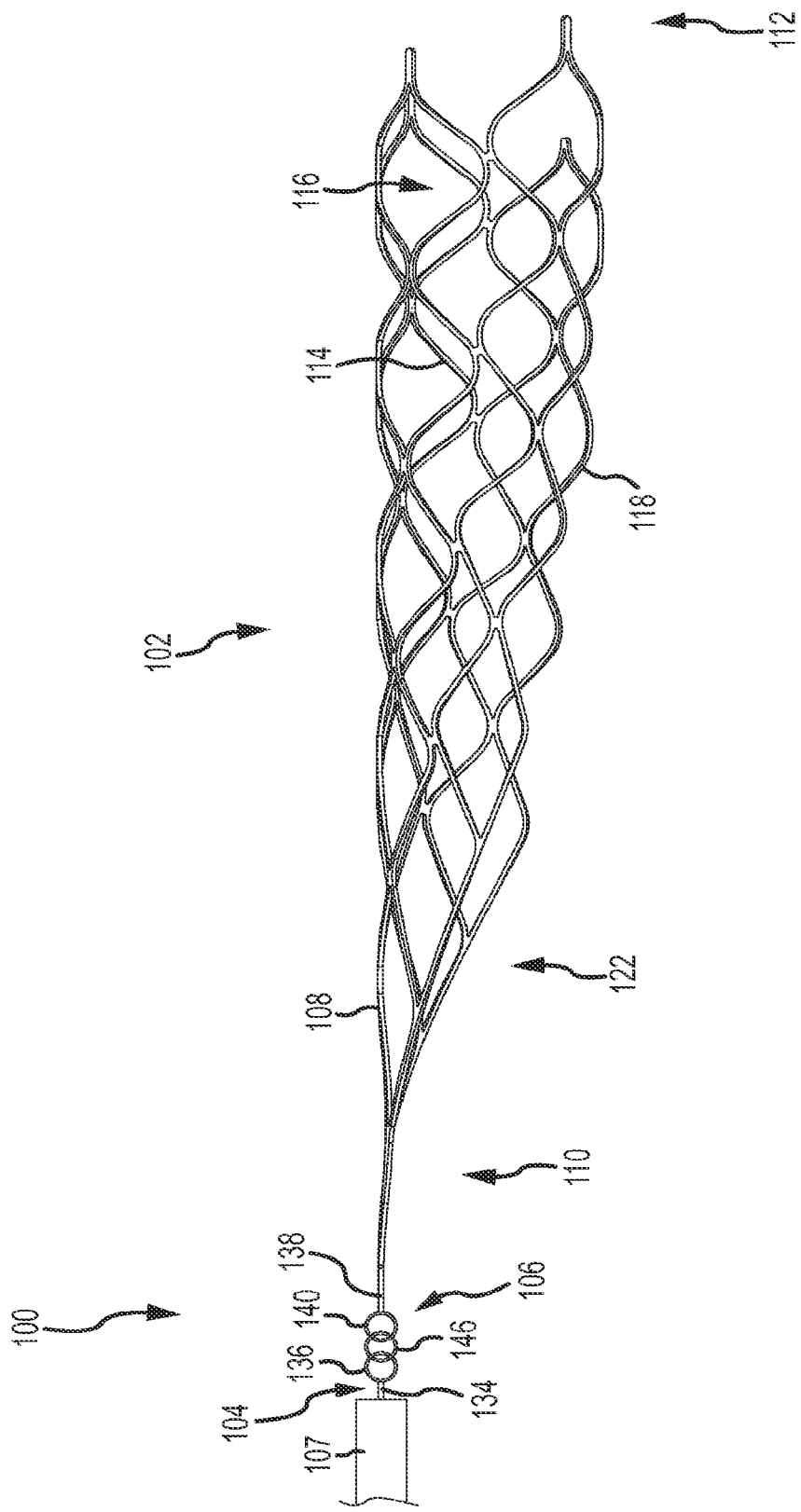
Figure 9:
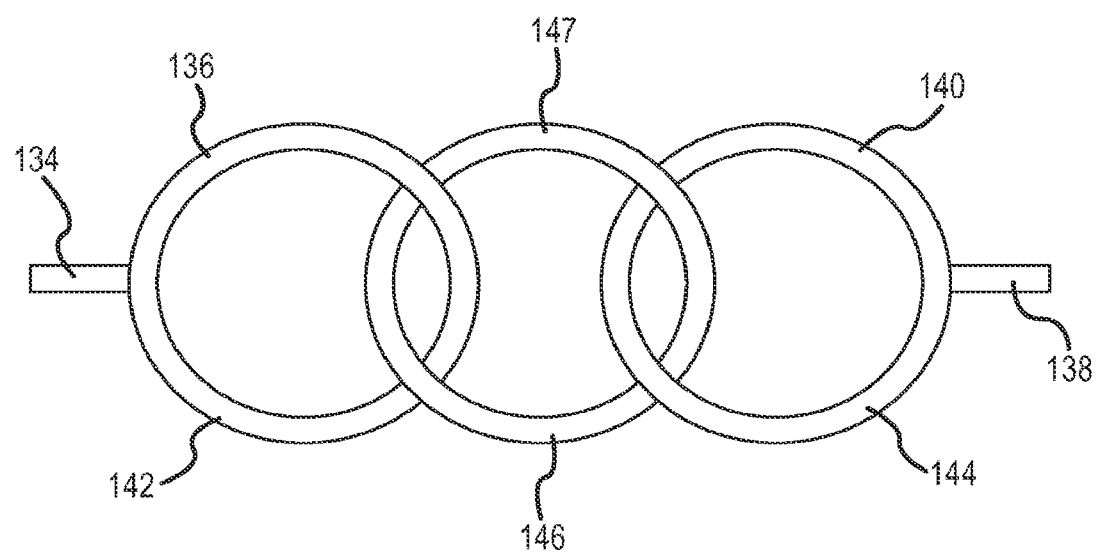

The first loop 142 can pass through an opening in the second loop 144 to directly interlink the first loop with the second loop, for example in the manner of links in a chain. In some embodiments, the first connection member 136 can be connected to the second connection member 140 by a third connection member 146, as illustrated, for example, in FIGS. 7 and 9. The third connection member 146 can comprise a third loop 147. The third connection member 146 can pass through an opening in each of the first loop 143 and the second loop 144 to directly interlink with each of the first loop with the second loop, for example in the manner of links in a chain. The third connection member 146 can be substantially circular in shape, as illustrated, for example, in FIGS. 7 and 9. The third connection member 146 can comprise a variety of shapes, such as, for example, circular, oval, teardrop, or polygonal, and optionally be formed as a generally rigid hoop or ring having any such shape. In some embodiments, the third connection member 146 can have the same shape as has one or both of the first connection member 136 and the second connection member 140. In some embodiments, the third connection member 146 can have a different shape than had by either of the first connection member 136 and the second connection member 140.

In some embodiments, the third connection member 146 can connect to the first connection member 136 and second connection member 140 such that the first connection member 136 can rotate relative to the second connection member 140 about an axis parallel to, generally parallel to, or coincident with a portion of a longitudinal axis of the medical device 100, the intervention member 102, the manipulation member 104, or an anatomical vessel. In some embodiments where the third connection member 146 connects to the first connection member 136 and second connection member 140 such that the first connection member 136 can rotate relative to the second connection member 140, the first connection member 136 can rotate relative to the second connection member 140 about the rotation axis over an infinite or a non-infinite range. In some embodiments, the third connection member 146 connects to the first connection member 136 and second connection member 140 such that the first connection member 136 can rotate relative to the second connection member 140 about the rotation axis over a range of angles of at least 360°, at least 540°, or at least 720°.

In some embodiments where the third connection member 146 connects to the first connection member 136 and second connection member 140 such that the first connection member 136 can rotate relative to the second connection member 140, the third connection member 146 permits the first connection member 136 to rotate relative to the second connection member 140 without deformation of one or both of the first connection member 136 and the second connection member 140. In some such embodiments, the first connection member 136 and the second connection member 140 can rotate relative to each other without plastic deformation of some or all of the first connection member 136, the second connection member 140, and the third connection member 136. In some embodiments, the first connection member 136 and the second connection member 140 can relatively rotate without one or both of resistance and restriction within the medical device 100 (e.g., between some or all of the first connection member 136, the second connection member 140, and the third connection member 136) apart from friction. In some embodiments, the first connection member 136 and the second connection member 140 can rotate relative to each other without deformation of the third connection member 146, and/or without plastic deformation of the third connection member 146.

Figure 10:
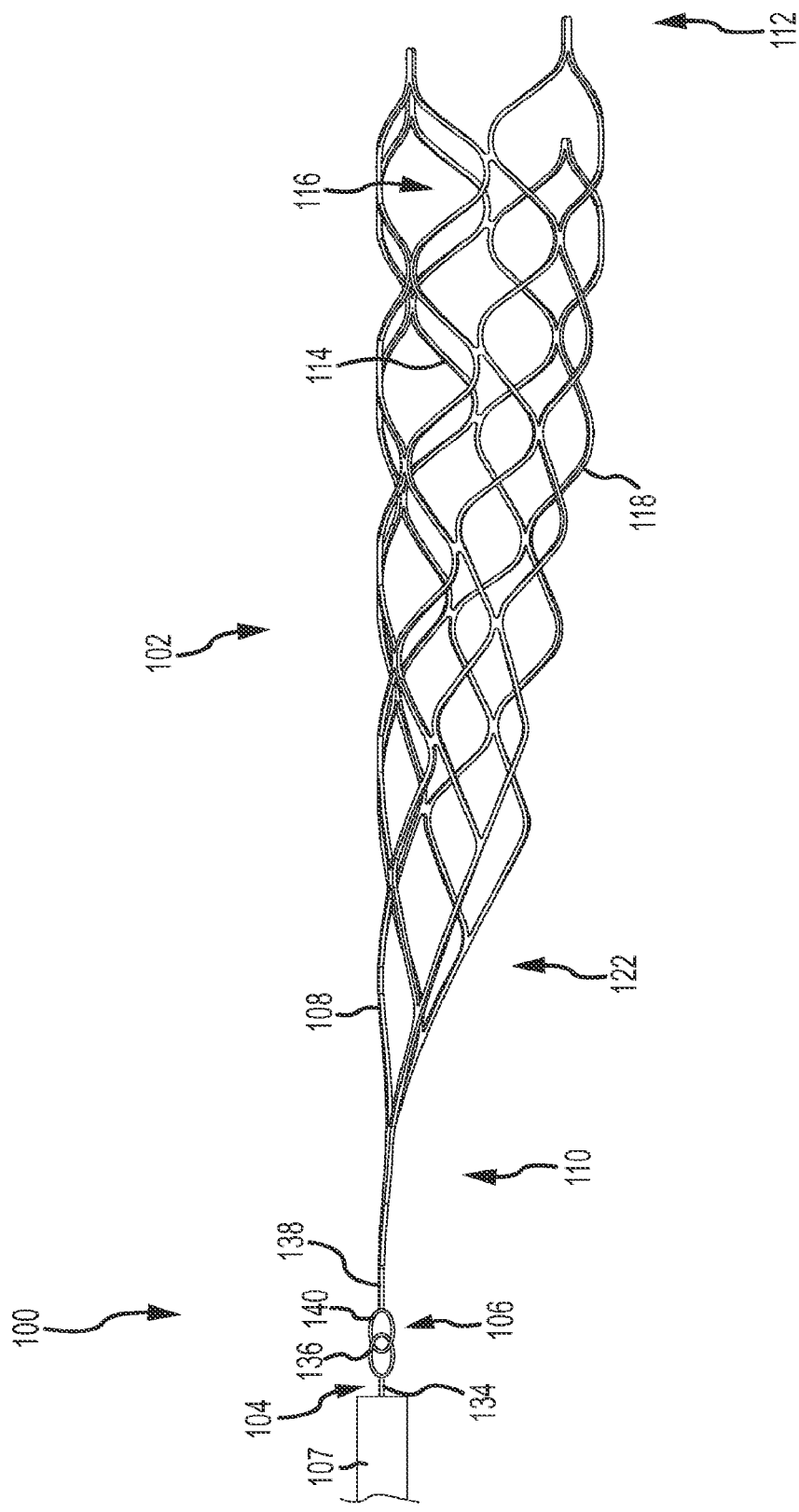
FIGS. 10 and 11 illustrate embodiments of a connection between an intervention member and a manipulation member that allows relative rotation therebetween.
Figure 11:
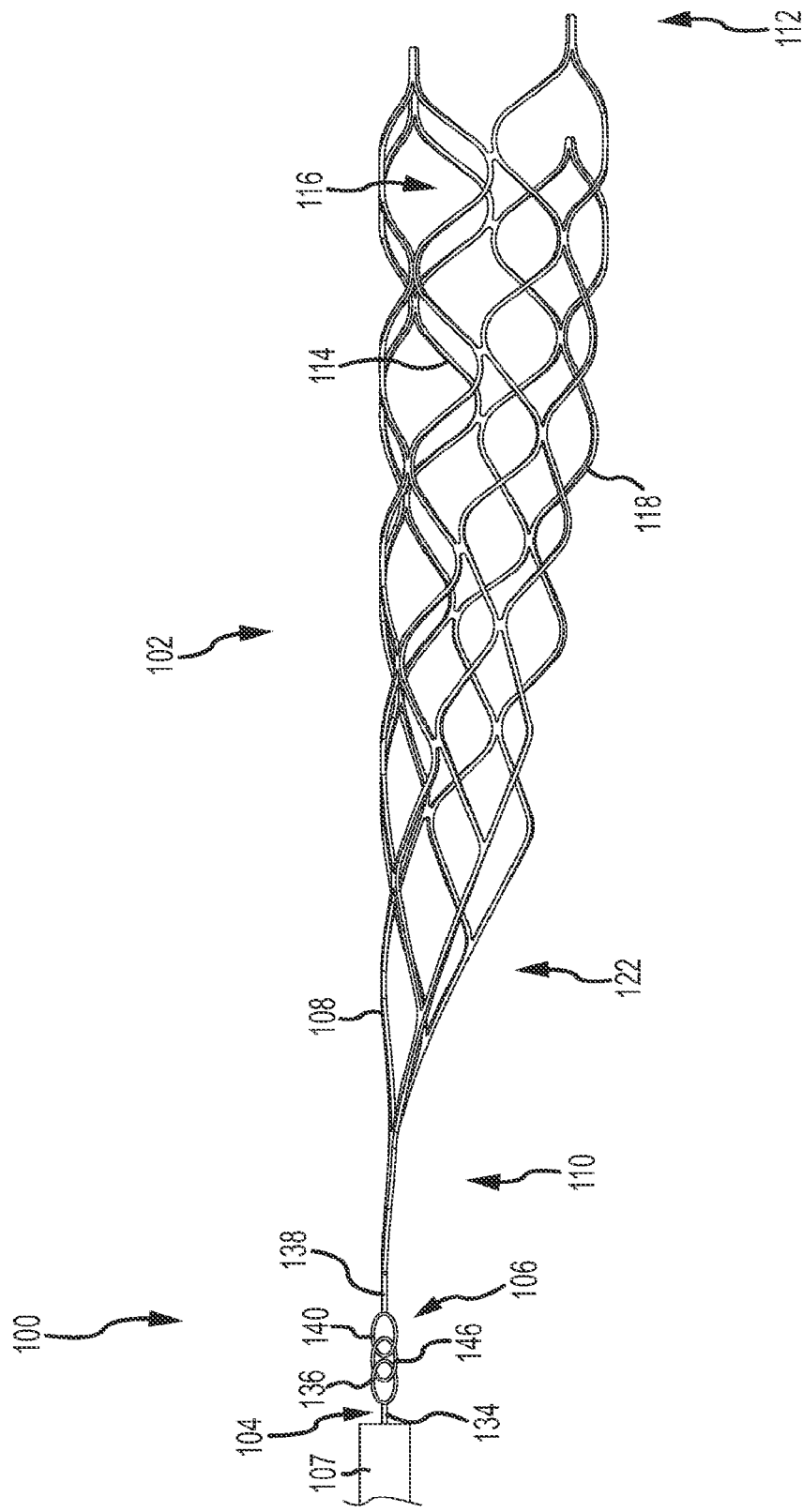
Figure 12:
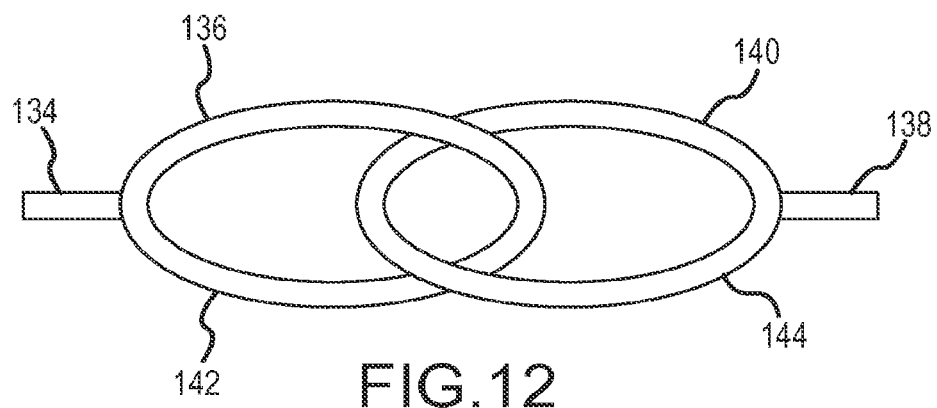
FIGS. 12 and 13 are schematic enlarged views of the connections of FIGS. 10 and 11, respectively.
Figure 13:
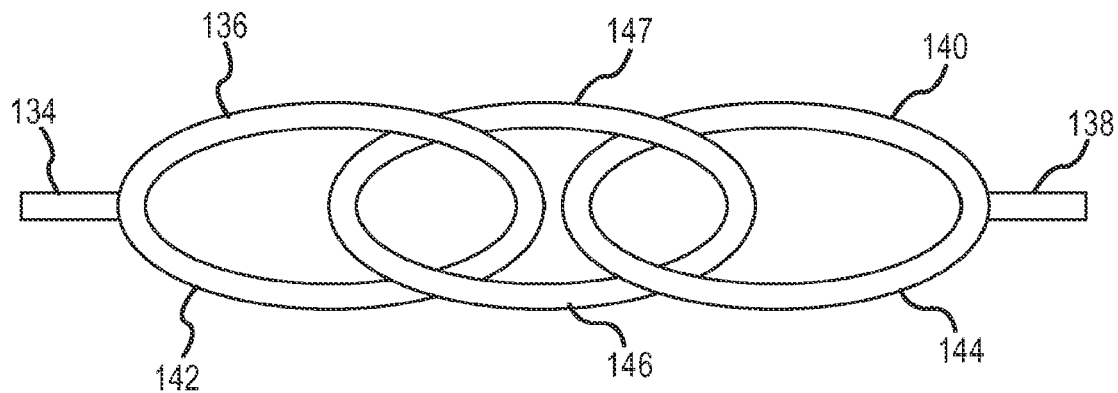

As illustrated, for example, in FIGS. 10 and 12, the first loop 142 and the second loop 144 can be substantially ovular in shape, and the first loop 142 can pass through an opening in and interlink with the second loop 144. As illustrated, for example, in FIGS. 11 and 13, the third connection member 146 can also be substantially ovular in shape, and can pass through openings in and interlink with the first connection member 136 and second connection member 140.

Figure 14:
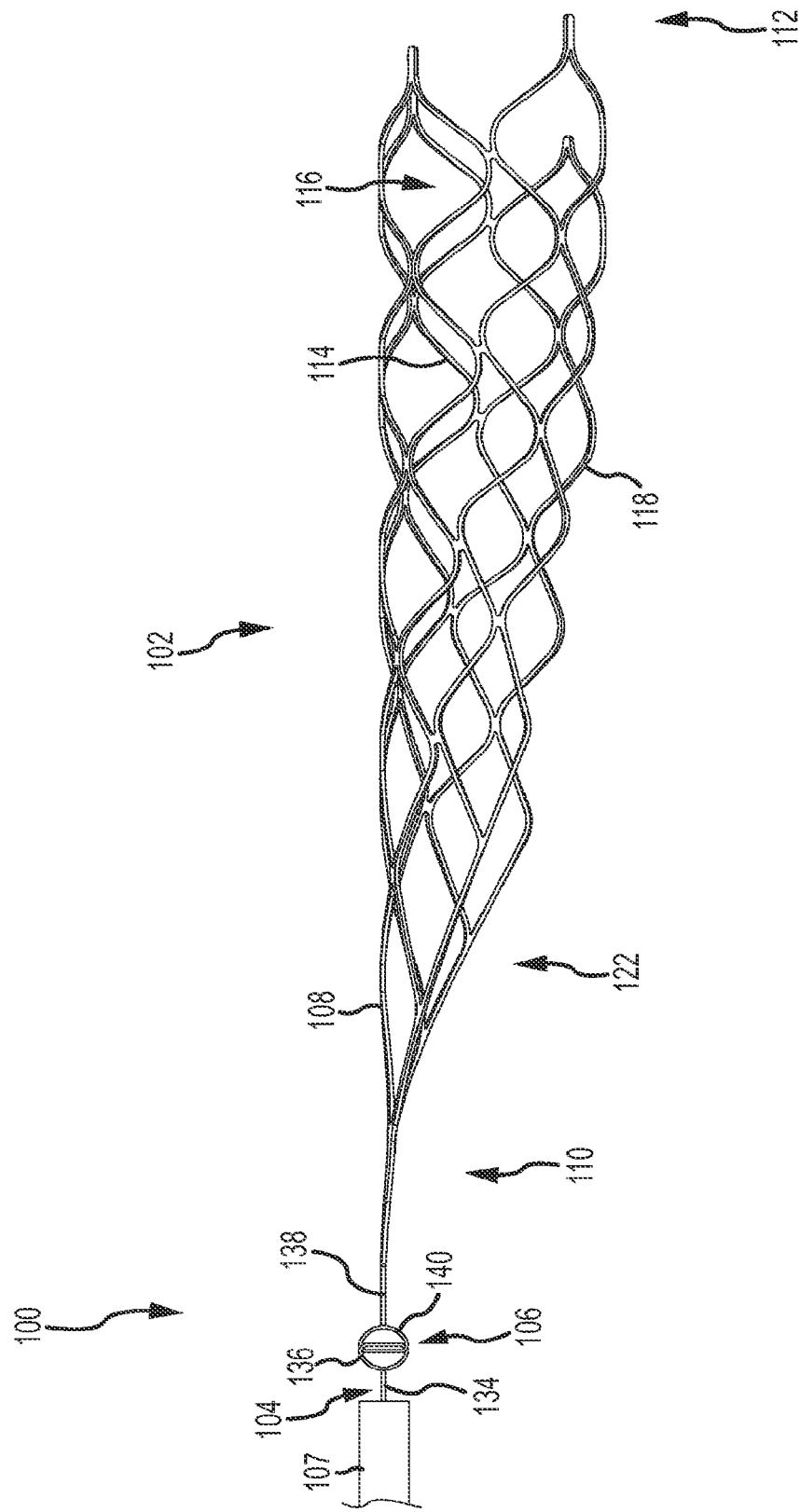
FIGS. 14 and 15 illustrate alternative embodiments of a connection between an intervention member and a manipulation member that allows relative rotation therebetween.
Figure 15:
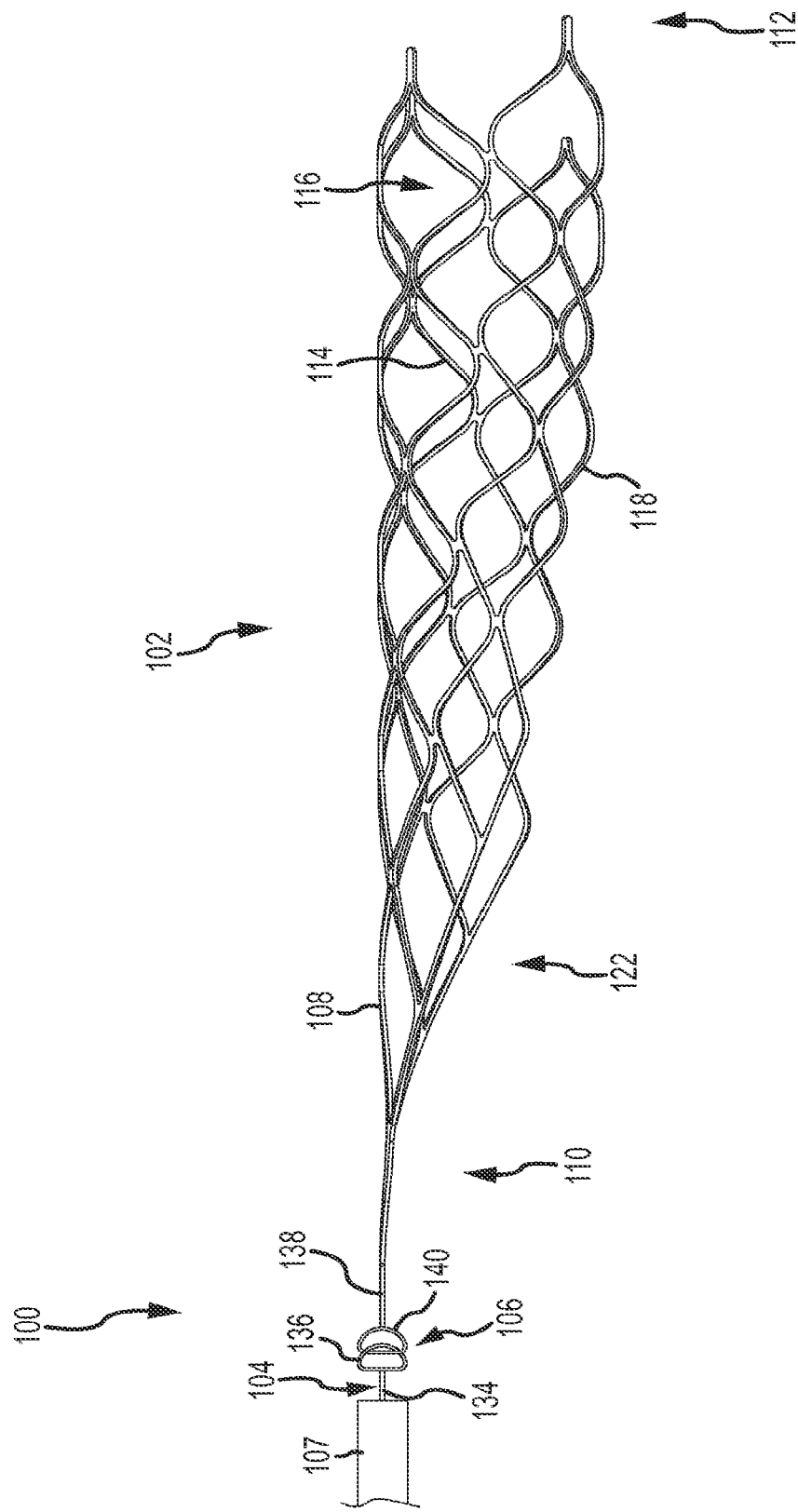
Figure 16:
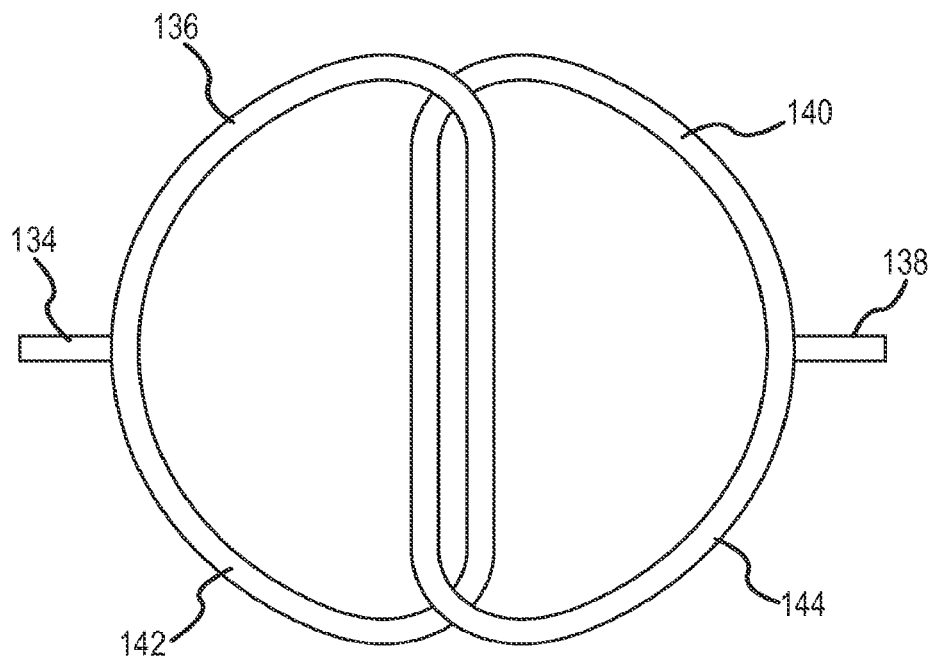
FIGS. 16 and 17 illustrate additional views of the connections of FIGS. 14 and 15, respectively.
Figure 17:
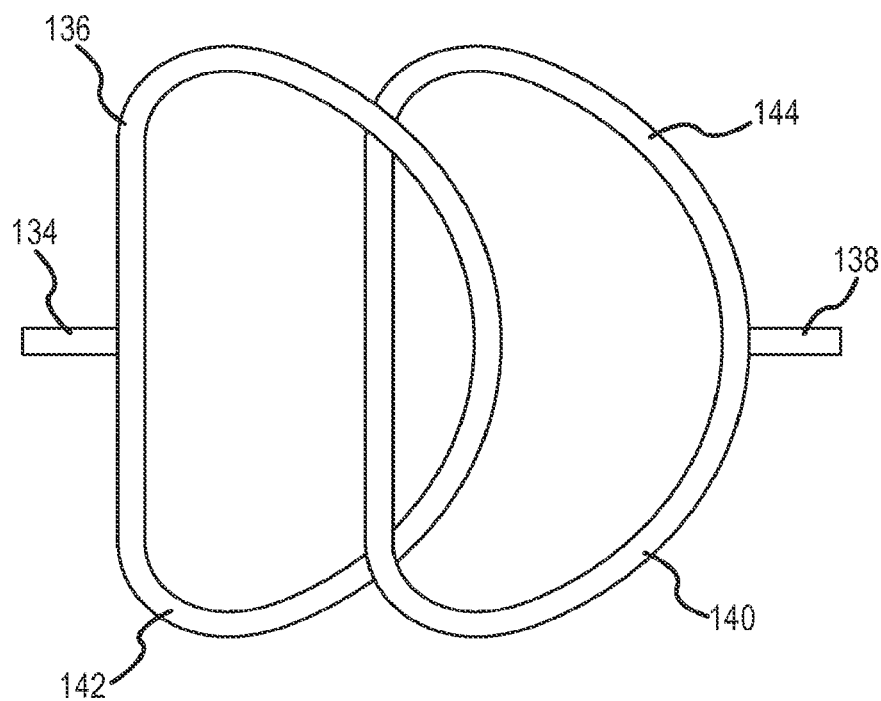

As illustrated, for example, in FIGS. 14 and 16, the first loop 142 and the second loop 144 can be have a shape comprising a arcuate section and a straight or substantially straight section joined by corners rounded to avoid damage to a biological vessel during use. In some embodiments, one of the first loop 142 and second loop 144 can have a shape comprising a substantially arcuate section and a substantially straight section, while the other of the first loop 142 and second loop 144 has a different shape. As illustrated in FIGS. 14 and 16, each of the first loop 142 and the second loop 144 can be arranged such that their arcuate portions are distal to each other while their substantially straight sections are proximal to each other. Alternatively, as illustrated in FIGS. 15 and 17, the first loop 142 and the second loop 144 can be arranged such that the arcuate portion of the first loop 142 is proximal to the straight section of the second loop 144.

Figure 18:
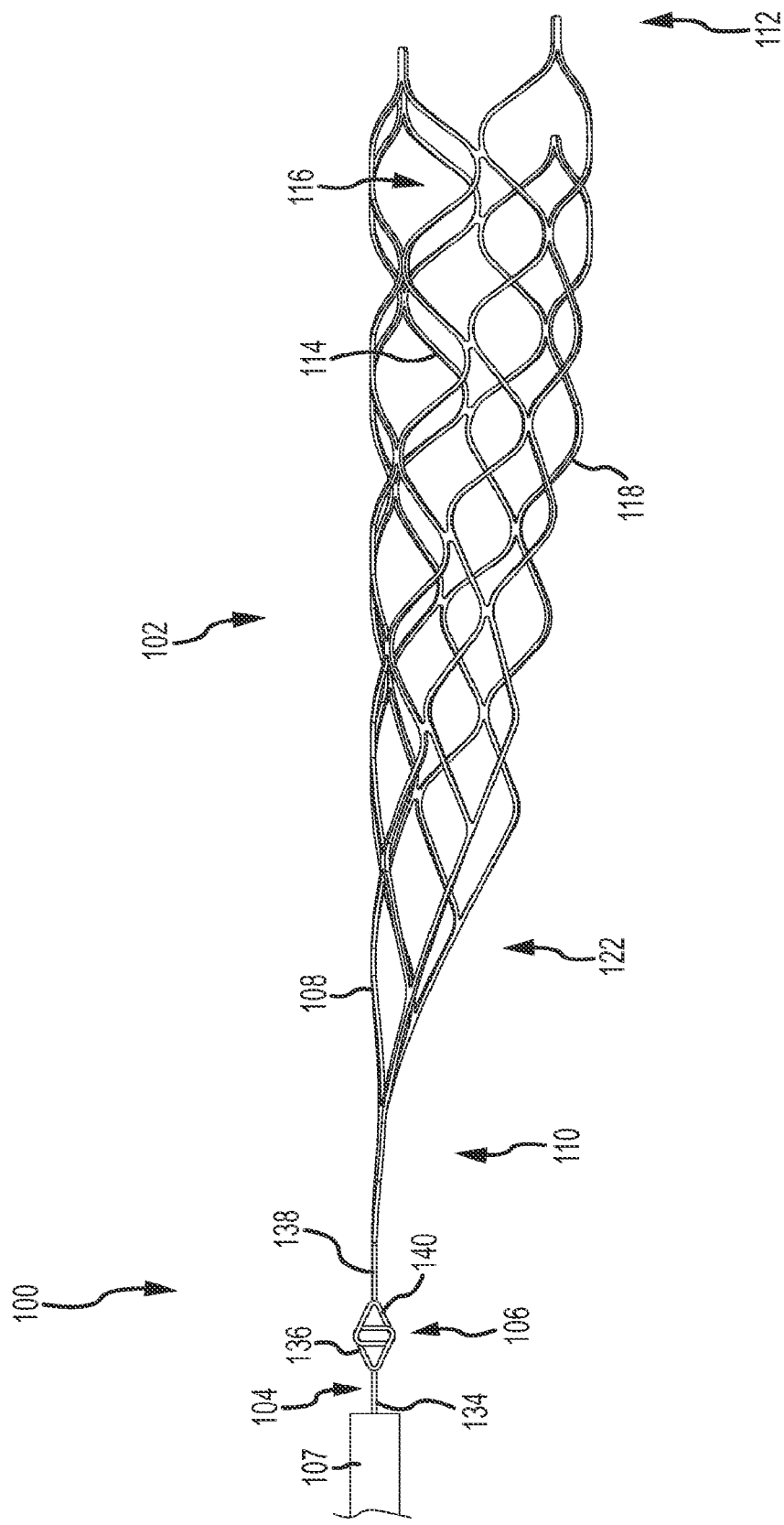
FIGS. 18 and 19 illustrate other embodiments of a connection between an intervention member and a manipulation member that allows relative rotation therebetween.
Figure 19:
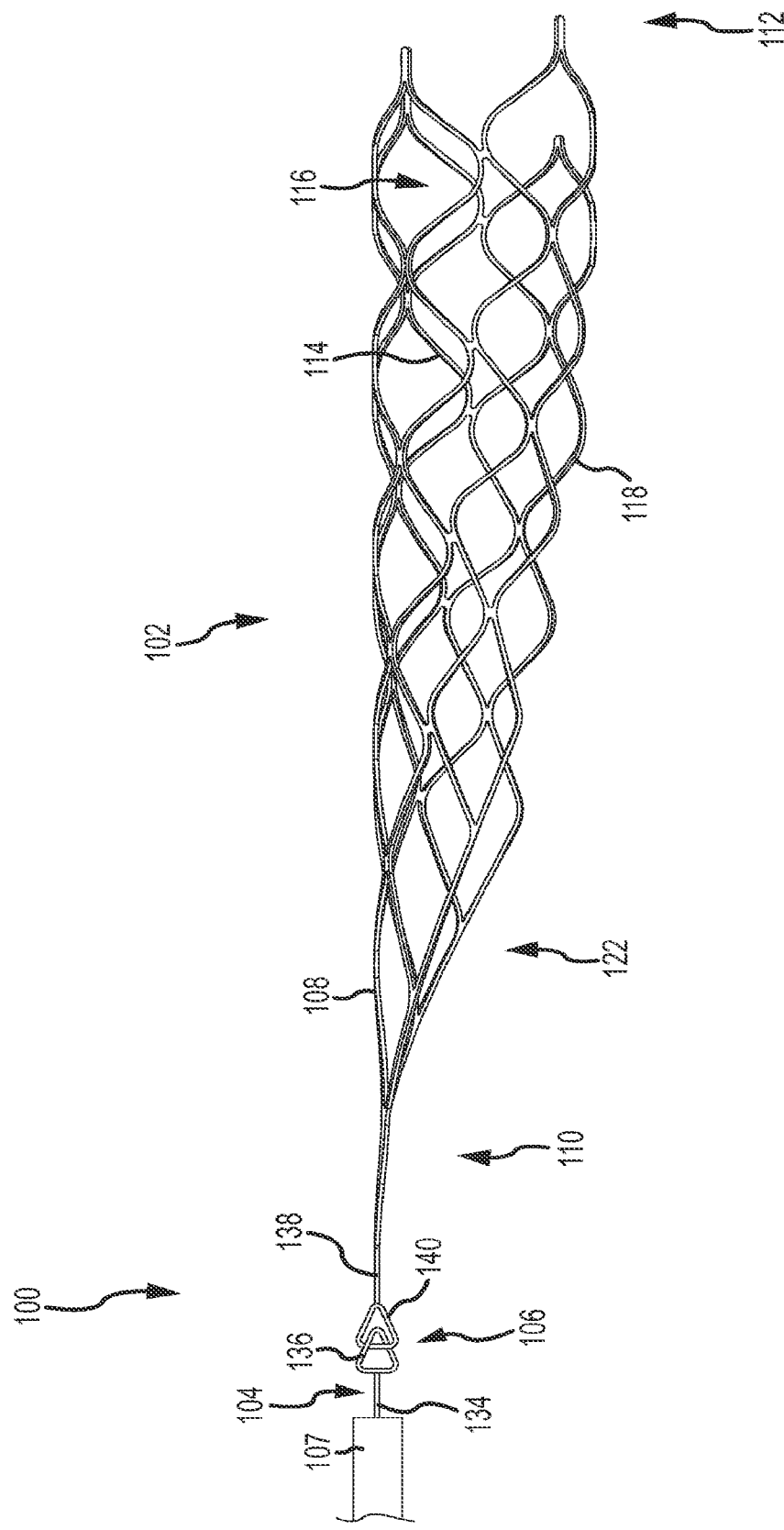
Figure 20:
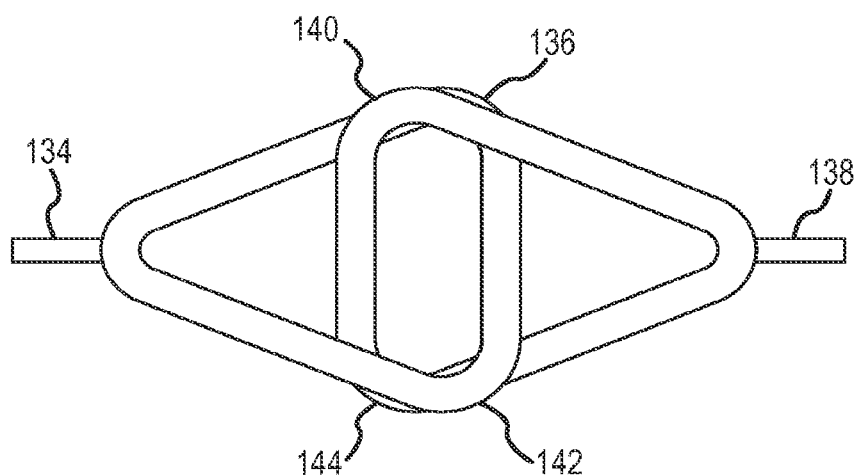
FIGS. 20 and 21 illustrate additional views of the connections of FIGS. 18 and 19, respectively.
Figure 21:
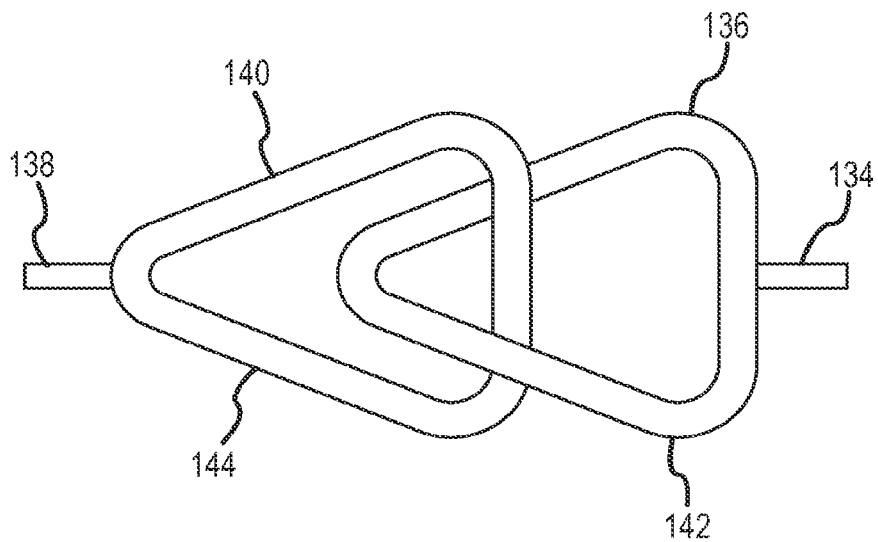

As illustrated, for example, in FIGS. 18 and 20, the first loop 142 and the second loop 144 can have a triangular or substantially triangular shape with corners rounded to avoid damage to a biological vessel during use. In some embodiments, each of the first loop 142 and the second loop 144 can have any polygonal shape with rounded corners. More specifically, in the embodiment shown in FIGS. 18 and 20, each of the first loop 142 and the second loop 144 can comprise three substantially straight sections joined by three substantially angled or rounded sections or corners. In some embodiments, one of the first loop 142 and second loop 144 can have a triangular or substantially triangular shape, while the other of the first loop 142 and second loop 144 can have a different shape. As illustrated in FIGS. 18 and 20, each of the first loop 142 and the second loop 144 can be arranged such that one of the substantially angled or rounded sections of each loop are distal to each other while one of the substantially straight sections of each loop are proximal to each other. Alternatively, as illustrated in FIGS. 19 and 21, the first loop 142 and the second loop 144 can be arranged such that a substantially angled or rounded section of the first loop 142 is proximal to a straight section of the second loop 144.

Figure 22:
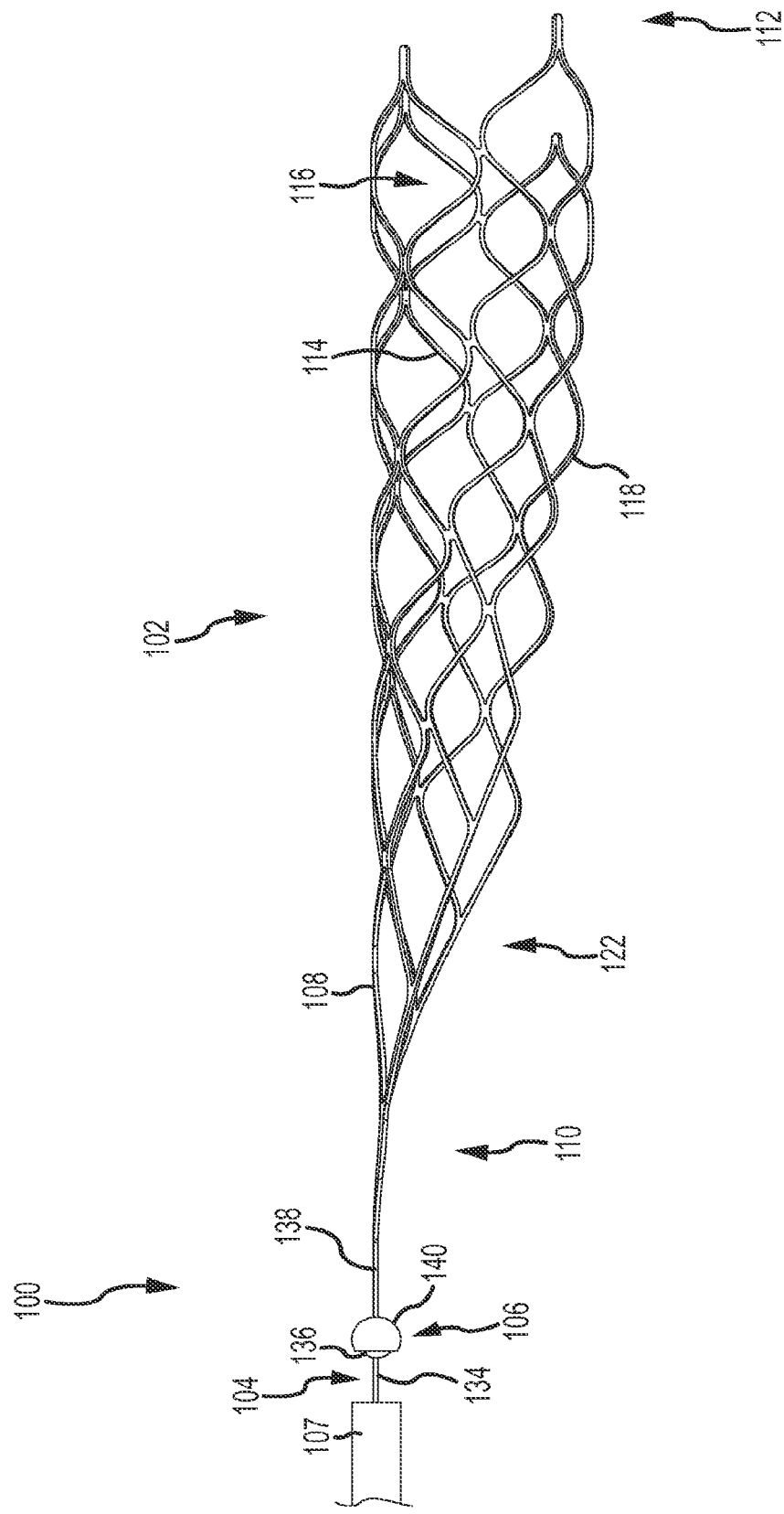
FIG. 22 illustrates an embodiment of a connection between an intervention member and a manipulation member that also allows relative rotation therebetween.
Figure 23:
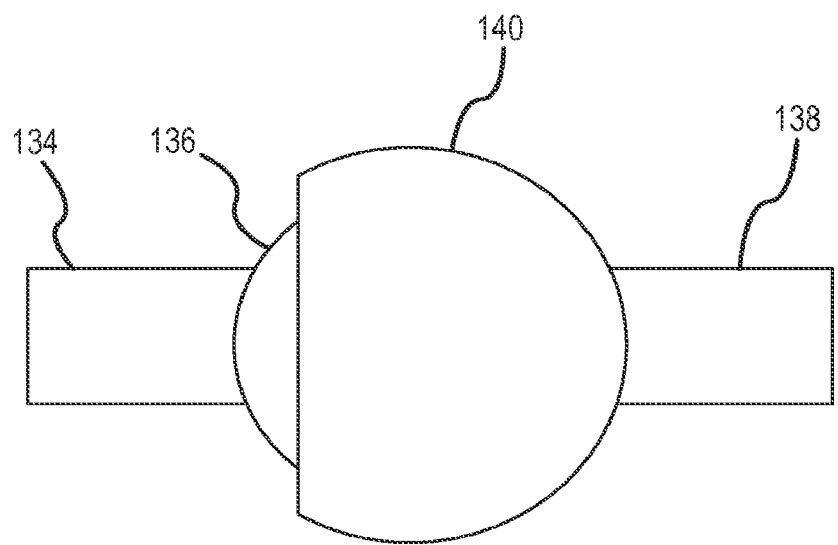
FIG. 23 is a schematic enlarged view of the connection of FIG. 22.

As illustrated, for example, in FIGS. 22 and 23, the first connection member 136 can comprise a ball and the second connection member 140 can comprise a socket. Alternatively, the first connection member 136 can comprise a socket and the second connection member 140 can comprise a ball.

Figure 24:
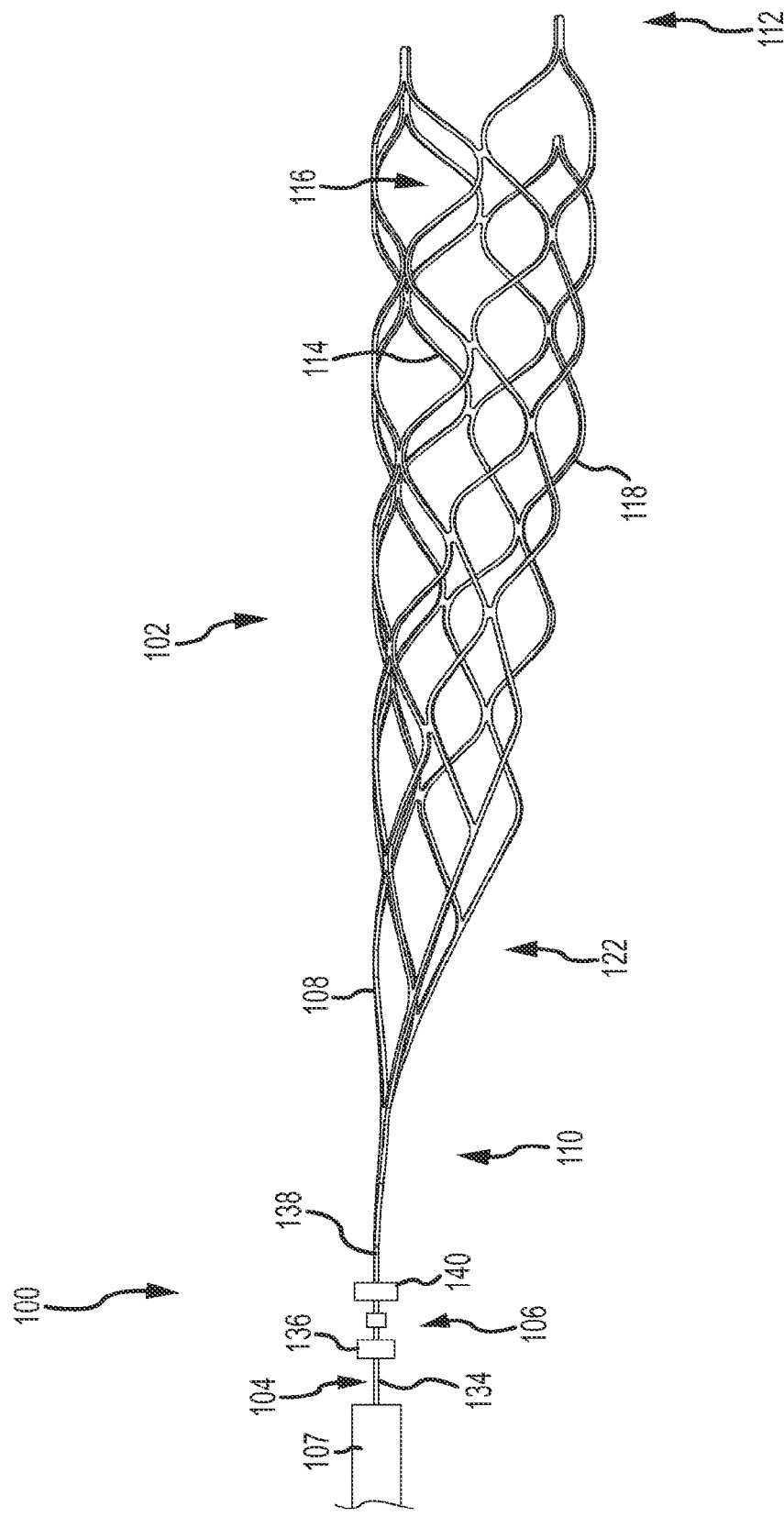
FIG. 24 illustrates an alternative embodiment of a connection between an intervention member and a manipulation member that allows relative rotation therebetween.
Figure 25:
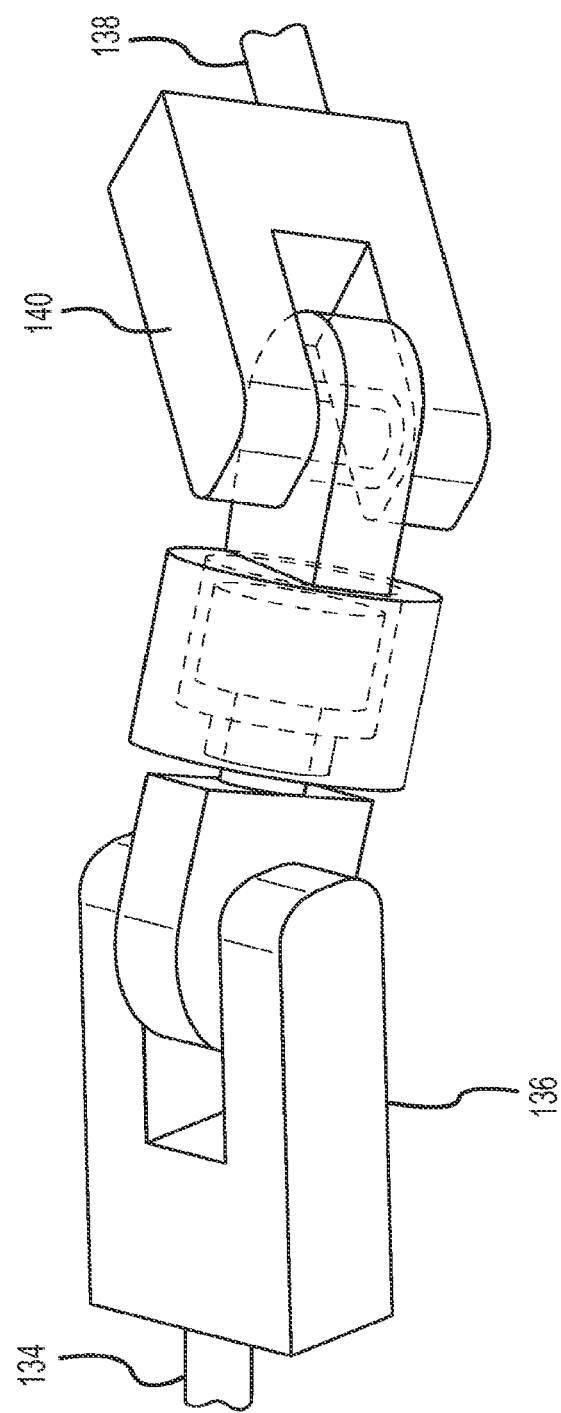
FIG. 25 is a schematic enlarged view of the connection of FIG. 24.

As illustrated, for example, in FIGS. 24 and 25, the connection 106 can comprise a universal joint. As illustrated in FIG. 24, the first connection member 136 can be a first universal joint element 150 and the second connection member 140 can be a second universal joint element 152.

Figure 26:
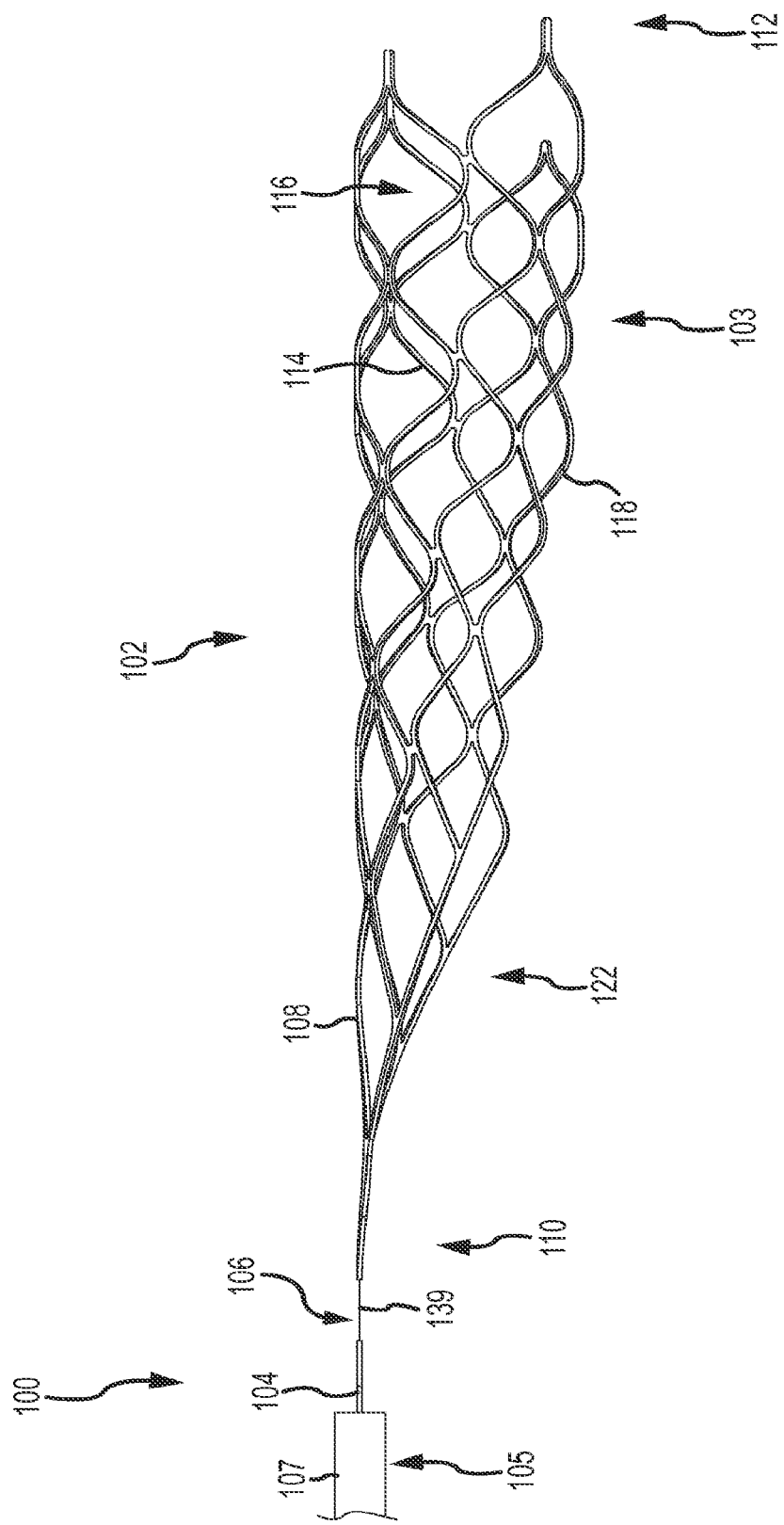
FIG. 26 illustrates another alternative embodiment of a connection between an intervention member and a manipulation member that allows relative rotation therebetween.
Figure 27:
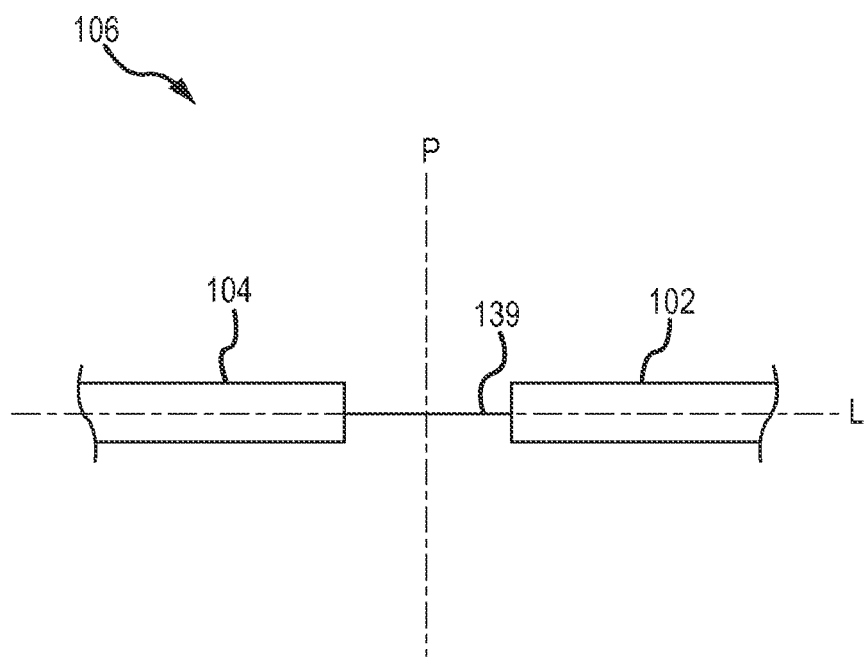
FIG. 27 is a schematic enlarged view of the connection of FIG. 26.

As illustrated, for example, in FIGS. 26 and 27, the connection 106 can comprise a filament 139 joined to each of and disposed between the manipulation member 104 and the intervention member 102. In some embodiments, the filament 139 can be devoid of any coil. In some embodiments, the filament 139 can be torquable about a longitudinal axis L and/or bendable about an axis P normal to the longitudinal axis L.

Figure 28:
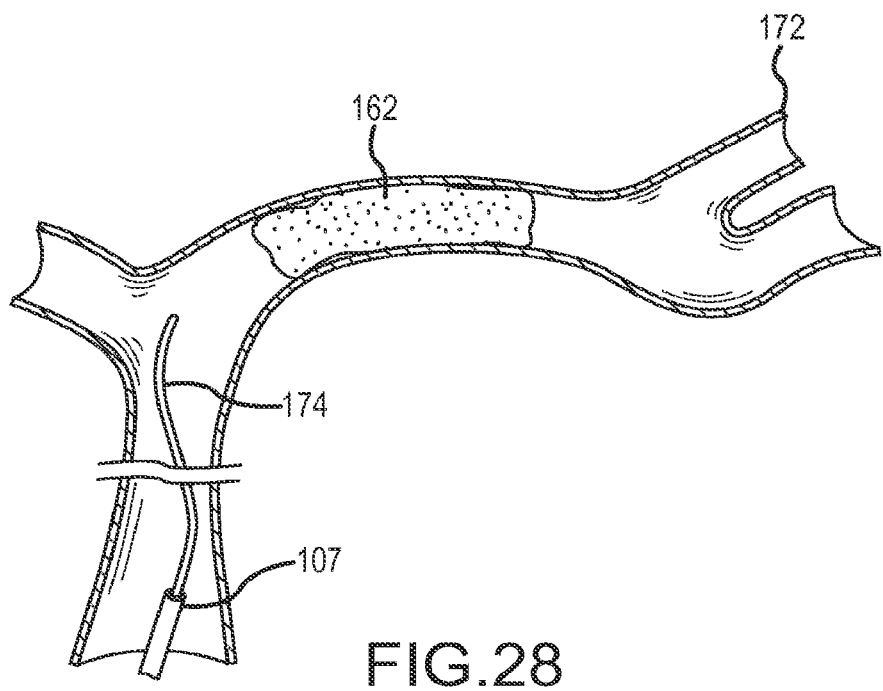
FIGS. 28-37 are cross-sectional views of a vessel and illustrate uses of a device according to some embodiments.
Figure 29:
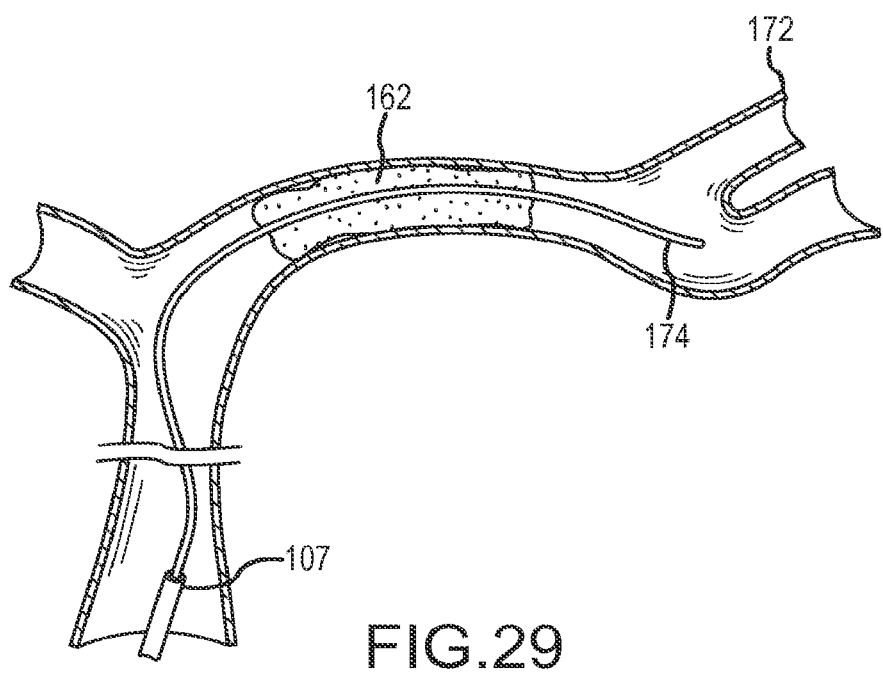
Figure 30:
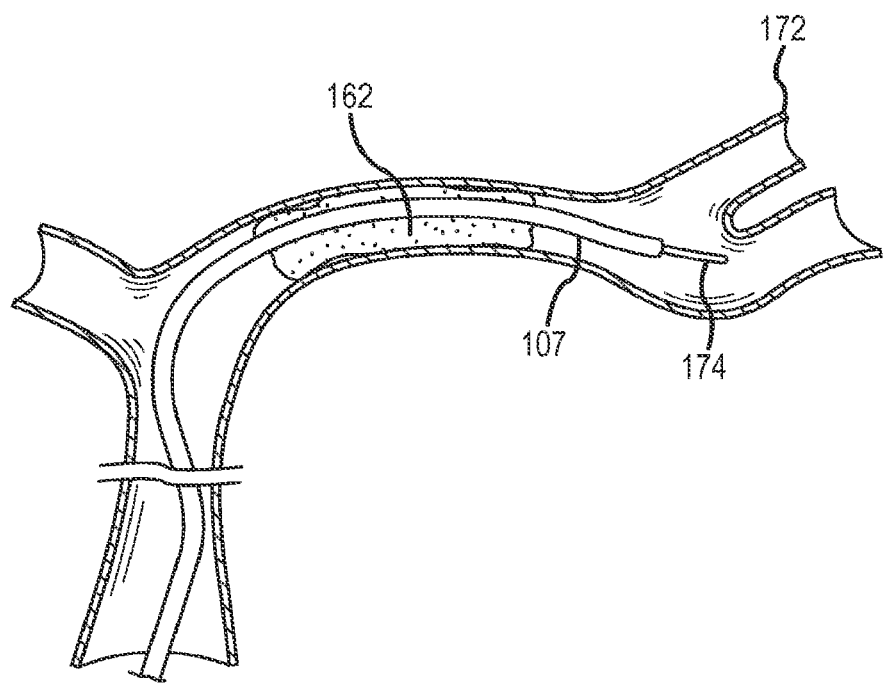

Methods for engaging and removing a thrombus 162 will now be discussed with reference to FIGS. 28-37. Referring to FIG. 28, the medical device 100 may be inserted into an anatomical vessel 172 by first inserting a guide wire 174 into the anatomical vessel 172. The inserted medical device 100 can be any embodiment of the medical device 100 disclosed herein, including any of the intervention members 102, elongate members 104, or connections 106. The guide wire 174 can be advanced through a guide catheter 164 (see FIG. 35), which optionally includes a balloon near the guide catheter's distal end, and a catheter 107 to the treatment site, adjacent the thrombus 162. Referring to FIG. 29, the guide wire 174 is advanced distally through the thrombus 162. Once the guide wire 174 is in position, the catheter 107 is advanced over the guide wire 174, through a distal end of the guide catheter, into the anatomical vessel 172. Referring to FIG. 30, the catheter 107 is advanced distally through the thrombus 162. The guide wire 174 is then withdrawn proximally.

Figure 31:
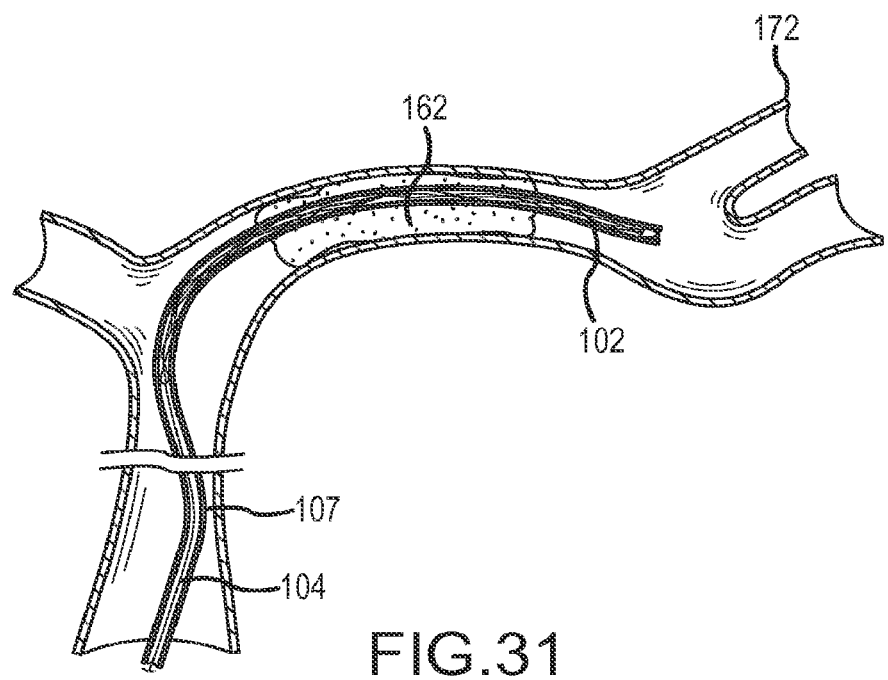

Referring to FIG. 31, the medical device 100 is advanced through the catheter 107 such that the distal end 112 of the medical device 100 is disposed distal of the thrombus 162 in the anatomical vessel 172. The medical device 100 is advanced through the catheter 107 by the manipulation member 104 coupled to the proximal end of the intervention member 102. The catheter 107 compresses the intervention member 102 and thus, maintains the intervention member 102 in a compressed, volume-reduced configuration as the intervention member 102 is advanced to the treatment site.

Figure 32:
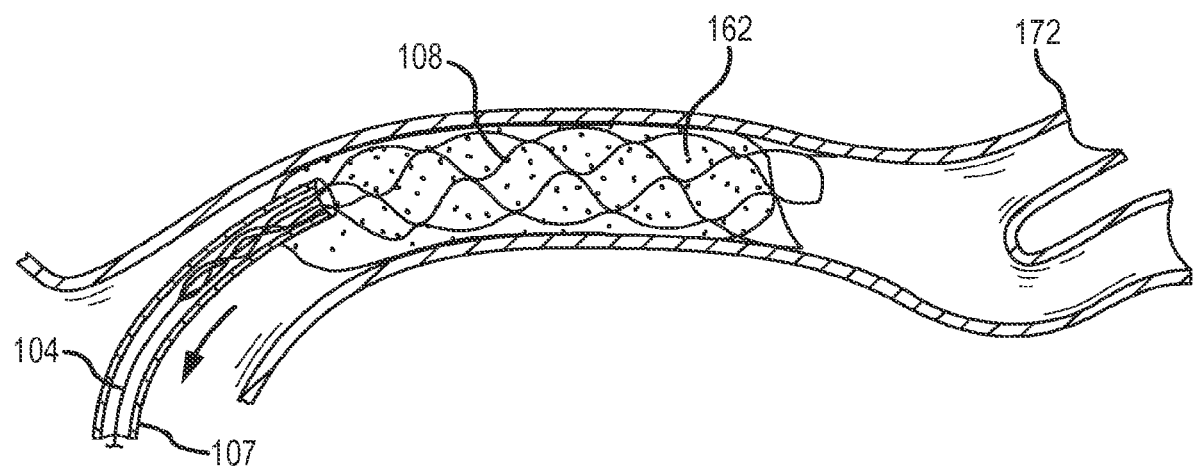
Figure 33:
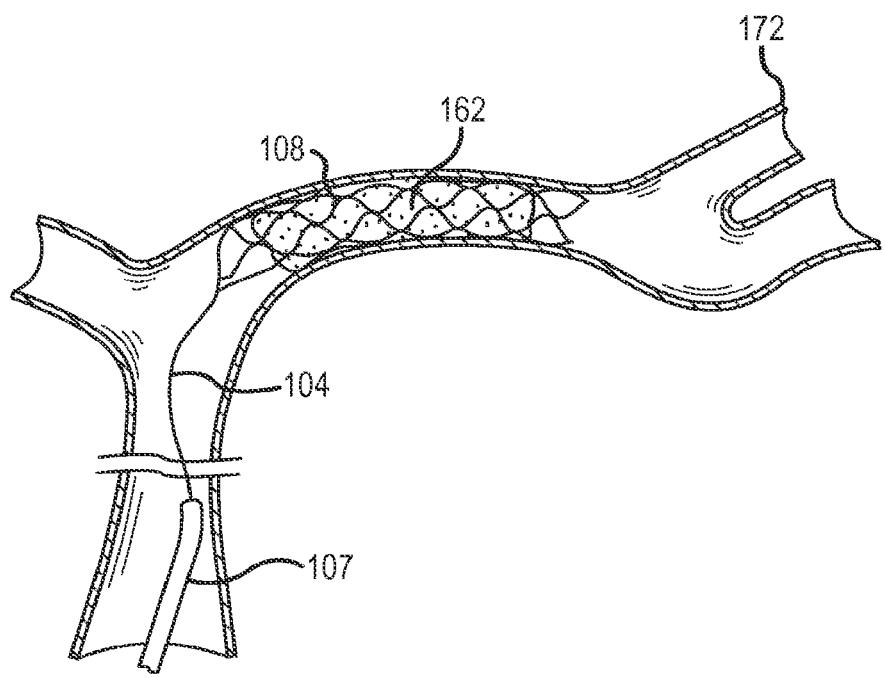

Referring to FIGS. 32 and 33, the catheter 107 is withdrawn proximally relative to the intervention member 102 to expose the intervention member 102. If the intervention member 102 is self-expanding, retraction of the catheter 107 can permit the intervention member 102 to expand. The frame 108 expands against a length of the thrombus 162 and engages the thrombus 162. As discussed above, the frame 108 is configured to engage and remove thrombi. A period of time can be allowed to pass to allow blood to reperfuse the downstream area (if and/or when blood flow passing the thrombus is reestablished by the expanding intervention member creating a flow path through the thrombus), the intervention member 102 to penetrate the thrombus 162, or both.

Figure 34:
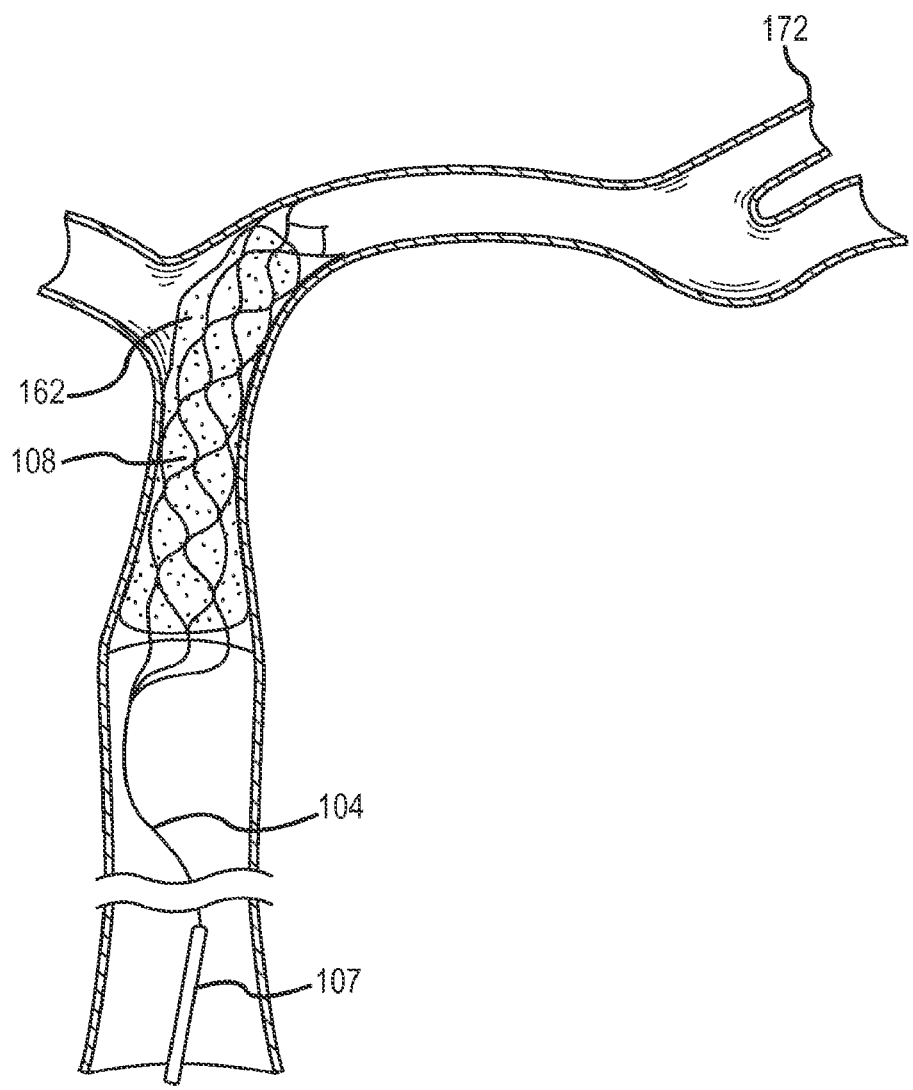
Figure 35:
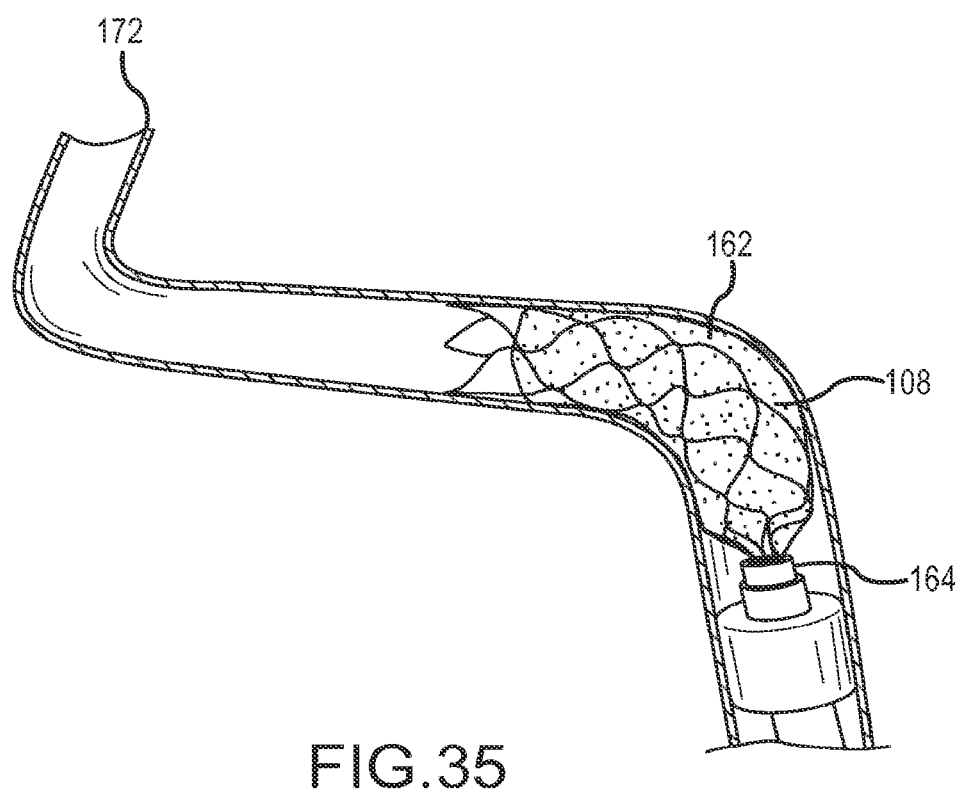

Referring to FIGS. 34 and 35, the intervention member 102 can be withdrawn proximally, along with the thrombus 162. As illustrated in FIG. 35, the intervention member 102 can be withdrawn proximally, along with the thrombus 162, into the guide catheter 164. In some embodiments, as the intervention member 102 is withdrawn proximally, the first connection member 136 can rotate relative to the second connection member 140 about an axis parallel to, generally parallel to, or coincident with a portion of a longitudinal axis of the medical device 100, the intervention member 102, the manipulation member 104, or an anatomical vessel. As the distal manipulation member end portion 134 can have the first connection member 136 and the proximal intervention member end portion 138 can have the second connection member 140, the manipulation member 104 and the intervention member 102 can also rotate relative to each other, in some embodiments. Instead of or in addition to the ability of the manipulation member 104 and the intervention member 102 to rotate relative to each other, the catheter 107 and the intervention member 102 can rotate relative to one another by virtue of the connection 106.

In some embodiments, as the intervention member 102 is withdrawn a distance, the distal manipulation member end portion 134 may translate and rotate relative to the anatomical vessel 172 about an axis parallel to, generally parallel to, or coincident with a portion of a longitudinal axis of the medical device 100, the intervention member 102, the manipulation member 104, or an anatomical vessel while the intervention member 102 translates (e.g., moves proximally along the vessel 172) and does not rotate, or rotates less than does the distal manipulation member end portion 134, relative to the anatomical vessel 172, as illustrated, for example, in FIGS. 33 and 34. A difference in the extent of rotation of the intervention member 102 compared to that of the distal manipulation member end portion 134, relative to the anatomical vessel 172, is enabled by relative rotation between the intervention member 102 and the manipulation member 104. Such relative rotation between the intervention member 102 and the manipulation member 104 may continue as the medical device 100 is withdrawn through the anatomical vessel 172. In some embodiments, the proximal end of intervention member 102 and the distal end of the manipulation member 104 can rotate relative to each other by at least 360°, at least 540°, or at least 720°.

Accordingly, any rotation of the manipulation member 104 (or the end portion 134 thereof), and/or the catheter 107, that occurs during retraction of the deployed/expanded intervention member 102 and/or catheter 107 along the vessel 172 is not transferred to the intervention member 102 (or only a reduced portion of such rotation is transferred to the intervention member 102). It has been found that advancement of an elongate member such as the manipulation member 104 and/or catheter 107 into tortuous vasculature can cause it to twist, and retracting the elongate member from such tortuous vasculature can cause it to un-twist, resulting in rotation during retraction. By reducing or preventing rotation of the intervention member 102 as it is withdrawn, the connection 106 can help reduce trauma to the vessel 172 as a result of a procedure performed with the medical device 100. Advantageously, the connection 106 helps reduce trauma in this manner regardless of whether the source of rotation during retraction is the manipulation member 104, the catheter 107, or a combination of the two.

The relative rotation between the intervention member 102 and the manipulation member 104 can continue until a limit of relative rotation is reached, in embodiments where an upper limit of relative rotation exists. In some embodiments, the proximal end of intervention member 102 and the distal end of the manipulation member 104 can rotate no more than 360°, no more than 540°, no more than 720°, or no more than 1080°. In embodiments where no upper limit of relative rotation exists, the intervention member 102 and the manipulation member 104 may relatively rotate indefinitely as the medical device 100 is withdrawn.

Figure 36:
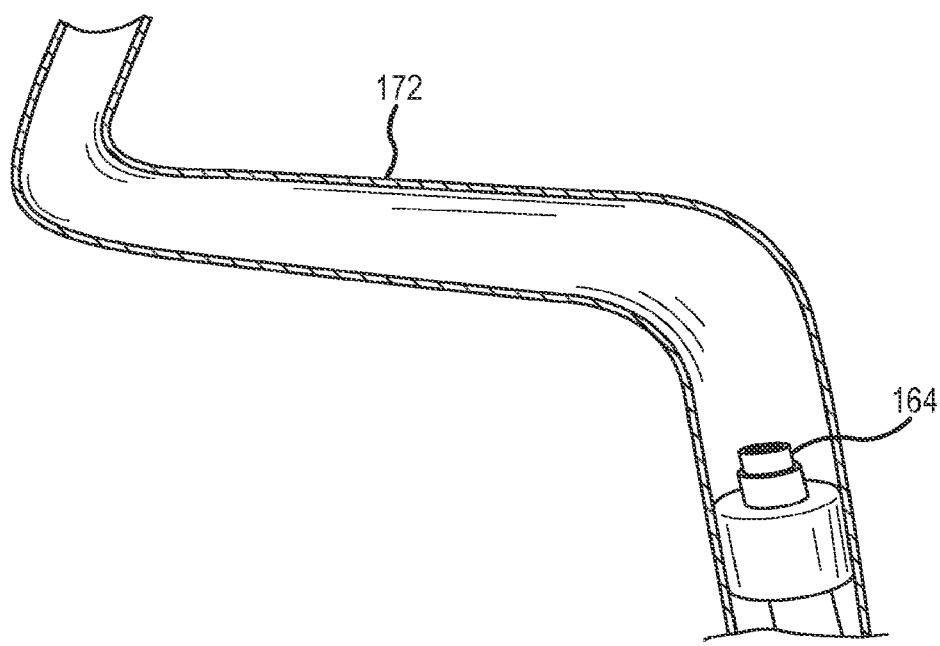

Referring to FIGS. 35 and 36, in embodiments wherein the guide catheter 164 comprises a balloon 168, the balloon optionally can be inflated to occlude flow during retraction of the thrombus 162 toward the guide catheter. In some embodiments, an aspiration syringe 170 can be attached to the guide catheter 164, and aspiration can be applied to aid thrombus retrieval.

Figure 37:
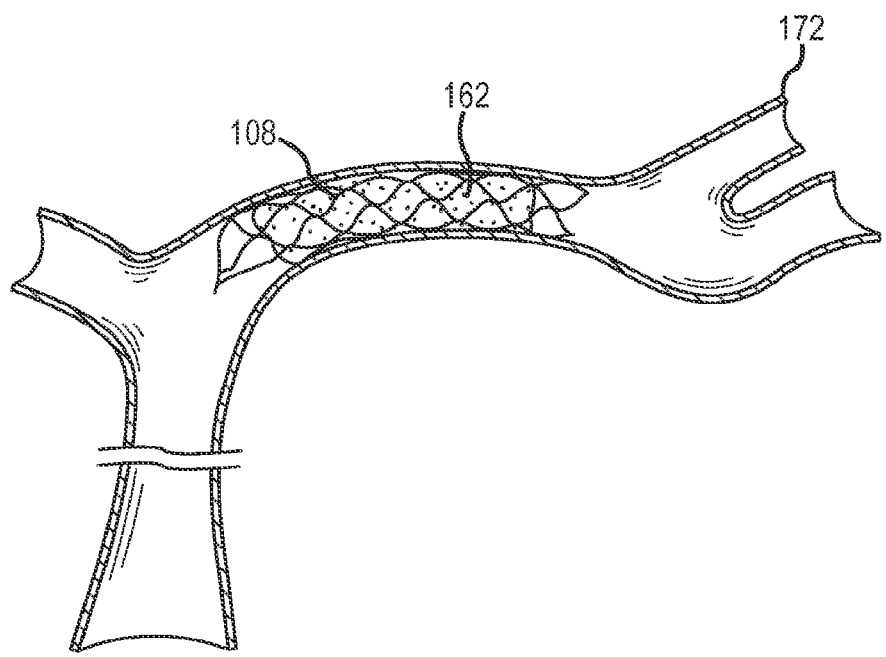

Referring to FIG. 35, the intervention member 102 is withdrawn proximally to the guide catheter 164. The guide catheter 164 causes the frame 108 to collapse, with the thrombus 162 engaged therein. The thrombus 162 is thus retrieved and removed from the anatomical vessel 172. Referring to FIG. 37, if retrieval of the intervention member 102 is determined to be undesirable, e.g., to avoid damaging the vessel 172, and the intervention member 102 is detachably or releasably connected to the manipulation member 104, the intervention member 102 can be detached from the manipulation member 104 and can remain in the vessel 172.

Additionally, while the intervention member 102 described above has been described in the context of use during a blood flow restoration procedure, the intervention member 102 can also, or alternatively, be used as an implantable member (e.g. stent). For example, the intervention member 102 can be released through the connection 106 at a stenosis, aneurysm, or other appropriate location in a vessel. The intervention member 102 can expand and engage a vessel wall so as to hold the vessel wall open and/or act as an occluding member. While the filament thicknesses, widths, cell sizes, and forces described above can be optimized for an intervention member 102 for flow restoration, these values can also be optimized for an intervention member 102 for use as an implantable member. In some embodiments the same values can be used for both flow restoration and use as an implantable member.

Figure 38:
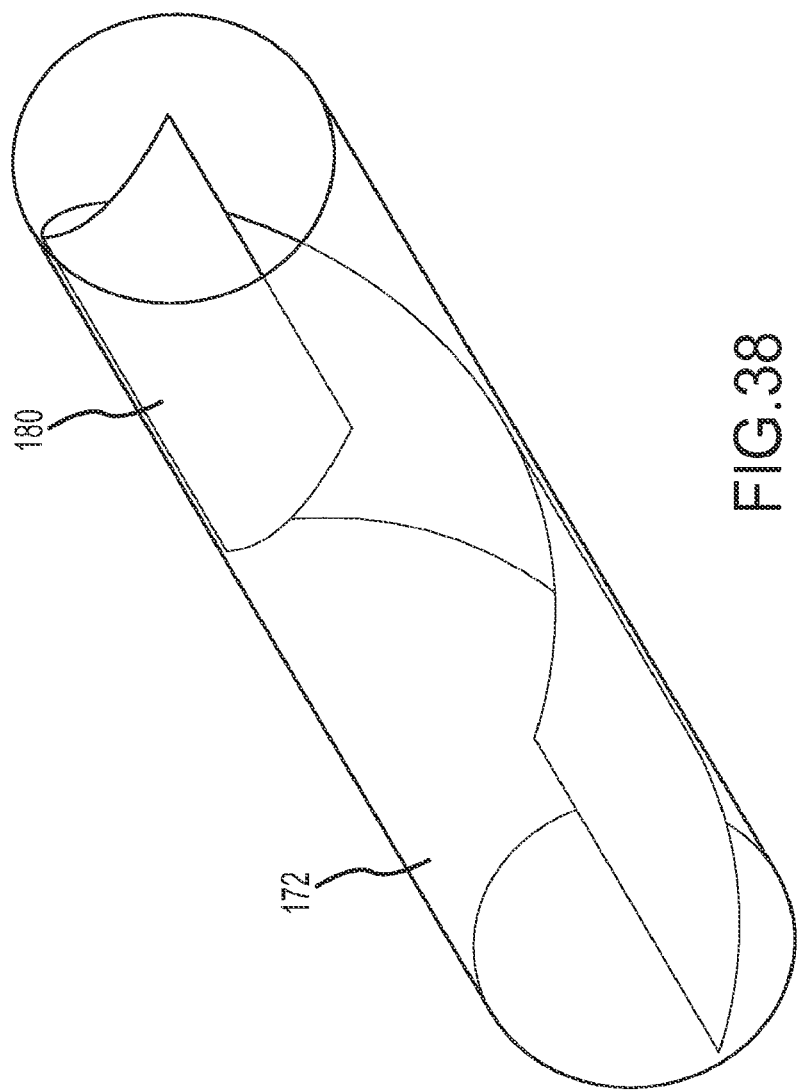
FIG. 38 schematically illustrates a zone of contact between an object and an interior wall of an anatomical vessel as the object travels through the vessel while rotating relative to the vessel.

FIG. 38 illustrates an area of contact 180 between a surface of an object and a vessel wall while translating through an anatomical vessel 172 and continuously rotating relative thereto about an axis parallel to, generally parallel to, or coincident with a portion of a longitudinal axis of the medical device 100, the intervention member 102, the manipulation member 104, or an anatomical vessel while in contact with the vessel wall. As a rate of rotation of the object per unit distance of translation increases, the area of contact 180 also increases. As the area of contact increases, a risk and extent of damage to the vessel wall can increase, and a risk of disengagement of some or all of an engaged thrombus can increase. The potential for and extent of rotation of a distal end of the manipulation member 104 can be greater in tortuous vessels, such as those of the neurovasculature. In some embodiments, relative rotation between the first connection member 136 and second connection member 140, or between a distal end of the manipulation member 104 (and/or a distal end of the catheter 107) and a proximal end of the intervention member 102, can (i) diminish a risk of the intervention member 102 losing engagement with, or hold upon, some or all of the thrombus 162, (ii) can reduce a risk or extent of damage to an interior wall of an anatomical vessel 172 during the thrombus retrieval, or (iii) both (i) and (ii).

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A medical device configured to perform an endovascular therapy, the device comprising:
    an elongate manipulation member;
    a first connection member coupled to a distal end portion of the elongate manipulation member;
    an intervention member comprising a plurality of struts defining a plurality of closed cells;
    a second connection member coupled to the intervention member; and
    a third connection member coupled to the first connection member and the second connection member such that the first connection member can rotate relative to the second connection member about a longitudinal axis of the device within a non-infinite range without deformation of at least one of the first connection member, the second connection member, or the third connection member,
    wherein the third connection member comprises a rigid material, and
    wherein the first connection member, the second connection member, and the third connection member are substantially permanently interlinked.

2. The medical device of claim 1, wherein the first and second connection members each comprise a rigid material.

3. The medical device of claim 1, wherein the elongate manipulation member comprises the first connection member such that the elongate manipulation member and the first connection member share a continuous surface.

4. The medical device of claim 1, wherein the intervention member comprises the second connection member such that the intervention member and the second connection member share a continuous surface.

5. The medical device of claim 1, wherein the first connection member comprises a first loop, the second connection member comprises a second loop, and the third connection member comprises a third loop, the third loop being substantially permanently interlinked with the first and second loops.

6. The medical device of claim 1, wherein the third connection member has a different shape than that of the first connection member or the second connection member.

7. The medical device of claim 1, wherein the elongate manipulation member has a length of at least 100 centimeters.

8. The medical device of claim 1, wherein the first connection member can rotate relative to the second connection member within the non-infinite rotation range without plastic deformation of at least one of the first connection member or the second connection member.

9. The medical device of claim 1, wherein the non-infinite rotation range is at least 180 degrees, and wherein the first connection member can rotate relative to the second connection member about the longitudinal axis of the device within the non-infinite rotation range with neither resistance nor restriction within the medical device apart from friction.

10. The medical device of claim 1, wherein the non-infinite rotation range is no more than 1080 degrees.

11. The medical device of claim 1, wherein the first connection member is positioned proximally of the third connection member which is positioned proximally of the second connection member.

12. A medical device for removal of an occlusive thrombus from a blood vessel, the device comprising:
    an elongate manipulation member;
    a first connection member coupled to the elongate manipulation member;
    an intervention member including an expandable structure configured to transition from a collapsed configuration to an expanded configuration, the expandable structure comprising a mesh including a plurality of cells sized to penetrate into and capture thrombus upon expansion to the expanded configuration;
    a second connection member coupled to the intervention member; and
    a third connection member coupled to the first connection member and the second connection member such that the first connection member can rotate relative to the second connection member about a longitudinal axis of the device within a non-infinite rotation range without deformation of at least one of the first connection member, the second connection member, or the third connection member, wherein at least one of the first connection member, the second connection member, or the third connection member comprises a rigid material, and wherein the first connection member, the second connection member, and the third connection member are substantially permanently interlinked.

13. The medical device of claim 12, wherein each of the first connection member, second connection member, and third connection member comprises a rigid material.

14. The medical device of claim 12, wherein the first connection member is integrally formed as a portion of the elongate manipulation member.

15. The medical device of claim 14, wherein the second connection member is integrally formed as a portion of the intervention member.

16. The medical device of claim 12, wherein the elongate manipulation member has a length of at least 100 centimeters.

17. The medical device of claim 12, wherein the first connection member can rotate relative to the second connection member about the longitudinal axis of the device within a non-infinite rotation range without plastic deformation of at least one of the first connection member or the second connection member.

18. The medical device of claim 12, wherein the non-infinite rotation range is no more than 1080 degrees.

19. A method for removing thrombus from a blood vessel, the method comprising:

advancing, via a catheter, a medical device toward a treatment site adjacent a thrombus within a blood vessel, the device comprising— an elongate manipulation member;
a first connection member coupled to the elongate manipulation member;
an intervention member;
a second connection member coupled to the intervention member; and
a third connection member coupled to the first connection member and the second connection member such that the first connection member can rotate relative to the second connection member about a longitudinal axis of the device within a non-infinite rotation range without deformation of at least one of the first connection member, the second connection member, or the third connection member;

expanding the intervention member from a collapsed configuration to an expanded configuration into the thrombus;

capturing at least a portion of the thrombus with the intervention member; and pulling proximally the elongate manipulation member to retract the intervention member within the blood vessel such that the first connection member rotates relative to the second connection member within a non-infinite rotation range.

20. The method of claim 19, wherein the first connection member rotates relative to the second connection member without deformation of at least two of the first connection member, the second connection member, or the third connection member.

21. The method of claim 19, wherein the third connection member comprises a rigid material.

22. The method of claim 19, wherein the non-infinite rotation range is no more than 1080 degrees.

* * * * *

UNITED STATES PATENT AND TRADEMARK OFFICE
CERTIFICATE OF CORRECTION

PATENT NO. : 11,369,394 B2  
APPLICATION NO. : 16/709431  
DATED : June 28, 2022  
INVENTOR(S) : Davidson et al.

Page 1 of 1

It is certified that error appears in the above-identified patent and that said Letters Patent is hereby corrected as shown below:

On the Title Page

Item (74), in Column 2, in "Attorney, Agent, or Firm", Line 2, delete "Linicum" and insert -- Lincicum --, therefor.

Signed and Sealed this  
Sixth Day of September, 2022

Katherine Kelly Vidal  
*Director of the United States Patent and Trademark Office*